US006334856B1

(12) United States Patent
Allen et al.

(10) Patent No.: US 6,334,856 B1
(45) Date of Patent: Jan. 1, 2002

(54) MICRONEEDLE DEVICES AND METHODS OF MANUFACTURE AND USE THEREOF

(75) Inventors: Mark G. Allen, Atlanta; Mark R. Prausnitz, Decatur, both of GA (US); Devin V. McAllister, Holley, NY (US); Florent Paul Marcel Cros, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 09/316,229

(22) Filed: May 21, 1999

Related U.S. Application Data

(63) Continuation-in-part of application No. 09/095,221, filed on Jun. 10, 1998, now Pat. No. 6,193,700.

(51) Int. Cl.$^7$ ...................................................... A61M 5/00
(52) U.S. Cl. ........................... 604/191; 216/75; 604/272; 128/898
(58) Field of Search .............................. 604/272, 20, 22, 604/35, 46, 501, 506, 181, 183, 239, 261, 191, 186; 29/890.01, 890.1; 424/449, 483; 216/75, 100, 102; 128/898

(56) References Cited

U.S. PATENT DOCUMENTS

| 2,893,392 A | 7/1959 | Wagner et al. |
| 3,034,507 A | 5/1962 | McConnell et al. |
| 3,086,530 A | 4/1963 | Groom |

(List continued on next page.)

FOREIGN PATENT DOCUMENTS

| DE | 195 25 607 | 1/1997 |
| EP | 0497620 | 8/1992 |
| EP | 0 652 600 | 5/1995 |
| JP | 7-132119 | 5/1995 |
| JP | 7-196314 | 8/1995 |
| WO | WO 93/17754 | 9/1993 |
| WO | WO 96/37256 | 11/1996 |
| WO | WO 96/40365 | 12/1996 |
| WO | WO 96/41236 | 12/1996 |
| WO | WO 97/07734 | 3/1997 |
| WO | WO 98/00193 | 1/1998 |
| WO | 98/00194 | 1/1998 |
| WO | WO 98/28037 | 7/1998 |

(List continued on next page.)

OTHER PUBLICATIONS

"Single–crystal whiskers," *Biophotonics Int'l* p. 64 (Nov./Dec. 1996).

(List continued on next page.)

*Primary Examiner*—Anhtuan T. Nguyen
(74) *Attorney, Agent, or Firm*—Sutherland Asbill & Brennan, LLP

(57) ABSTRACT

Microneedle devices are provided for transport of therapeutic and biological molecules across tissue barriers and for use as microflameholders. In a preferred embodiment for transport across tissue, the microneedles are formed of a biodegradable polymer. Methods of making these devices, which can include hollow and/or porous microneedles, are also provided. A preferred method for making a microneedle includes forming a micromold having sidewalls which define the outer surface of the microneedle, electroplating the sidewalls to form the hollow microneedle, and then removing the micromold from the microneedle. In a preferred method of use, the microneedle device is used to deliver fluid material into or across a biological barrier from one or more chambers in fluid connection with at least one of the microneedles. The device preferably further includes a means for controlling the flow of material through the microneedles. Representative examples of these means include the use of permeable membranes, fracturable impermeable membranes, valves, and pumps.

24 Claims, 7 Drawing Sheets

U.S. PATENT DOCUMENTS

| | | |
|---|---|---|
| 3,123,212 A | 3/1964 | Taylor et al. |
| 3,136,314 A | 6/1964 | Kravitz |
| RE25,637 E | 9/1964 | Kravitz et al. |
| 3,221,739 A | 12/1965 | Rosenthal |
| 3,221,740 A | 12/1965 | Rosenthal |
| 3,556,080 A | 1/1971 | Hein |
| 3,596,660 A | 8/1971 | Melone |
| 3,675,766 A | 7/1972 | Rosenthal |
| 3,918,449 A | 11/1975 | Pistor |
| 3,964,482 A | 6/1976 | Gerstel et al. |
| 4,109,655 A | 8/1978 | Chacornac |
| 4,159,659 A | 7/1979 | Nightingale |
| 4,222,392 A | 9/1980 | Brennan |
| 4,771,660 A | 9/1988 | Yacowitz |
| 4,798,582 A | 1/1989 | Sarath et al. |
| 4,921,475 A | 5/1990 | Sibalis |
| 4,969,468 A | 11/1990 | Byers et al. |
| 5,054,339 A | 10/1991 | Yacowitz |
| 5,138,220 A | 8/1992 | Kirkpatrick |
| 5,250,023 A | 10/1993 | Lee et al. |
| 5,279,544 A | 1/1994 | Gross et al. |
| 5,279,552 A | 1/1994 | Magnet |
| 5,335,670 A | 8/1994 | Fishman |
| 5,364,374 A | 11/1994 | Morrison et al. |
| 5,383,512 A | 1/1995 | Jarvis |
| 5,401,242 A | 3/1995 | Yacowitz |
| 5,457,041 A | 10/1995 | Ginaven et al. |
| 5,527,288 A | 6/1996 | Gross et al. |
| 5,582,184 A | 12/1996 | Erickson et al. |
| 5,591,139 A * | 1/1997 | Lin et al. ............ 604/264 |
| 5,611,806 A | 3/1997 | Jang |
| 5,611,809 A | 3/1997 | Marshall et al. |
| 5,618,295 A | 4/1997 | Min |
| 5,658,515 A | 8/1997 | Lee et al. |
| 5,697,901 A | 12/1997 | Eriksson |
| 5,801,057 A | 9/1998 | Smart et al. |
| 5,843,114 A | 12/1998 | Jang |
| 5,879,326 A | 3/1999 | Godshall et al. |
| 6,050,988 A | 4/2000 | Zuck |

OTHER PUBLICATIONS

"101 Uses for Tiny Tubules," *Science* 247 (1990).

Amsden, et al., "Transdermal Delivery of Peptide and Protein Drugs: an Overview," *AIChE Journal* 41(8):1972–1997 (1995).

*Bronaugh & Maibach, *Percutaneous Absorption, Mechanisms—Methodology—Drug Delivery* (Marcel Dekker, New York 1989).

Brumlik, et al., "Template Synthesis of Metal Microtubules," *J. Am. Chem. Soc.* 113:3174–3175 (1991).

*Despont, et al., "High–Aspect–Ratio, Ultrathick, Negative–Tone Near–UV Photoresist for MEMS," *Proc. of IEEE 10th Annual International Workshop on MEMS*, Nagoya, Japan, pp. 518–522 (Jan. 26–30, 1997).

Edell, et al., "Factors Influencing the Biocompatibility of Insertable Silicon Microshafts in Cerebral Cortex," *IEEE Transactions on Biomedical Engineering* 39(6):635–43 (1992).

Frazier, et al., "Two dimensional metallic microelectrode arrays for extracellular stimulation and recording of neurons", IEEE Proceedings on the Micro Electro Mechanical Systems Conference, pp. 195–200 (1993).

Frazier, et al., "Metallic Microstructures Fabricated Using Photosensitive Polyimide Electroplanting Molds," *Journal of Microelectromechanical Systems* 2:87–97 (1993).

*Hadgraft & Guy, eds., *Transdermal Drug Delivery: Developmental Issues and Research Initiatives* (Marcel Dekker New York 1989).

Haga, et al., "Transdermal iontophoretic delivery of insulin using a photoetched microdevice," *J. Controlled Release* 43:139–49 (1997).

Hashmi, et al., "Genetic Transformation of Nematodes Using Arrays of Micromechanical Piercing Structures," *Bio Techniques* 19(5):766–70 (1995).

*Henry, et al., "Micromachined Needles for the Transdermal Delivery of Drugs," *Micro Electro Mechanical Systems,* Heidelberg, Germany, pp. 494–498 (Jan. 26–29, 1998).

*Henry, et al., "Microfabricated microneedles: A novel method to increase transdermal drug delivery," *J. Pharm. Sci.* 87:922–925 (1998).

*Hoffert, "Transcutaneous methods get under the skin," *The Scientist* 12 (1998).

*Jaeger, *Introduction to Microelectronic Fabrication* (Addison–Wesley Publishing Co., Reading MA 1988).

Jansen, et al., "The Black Silicon Method IV: The Fabrication of Three–Dimensional Structures in Silicon with High Aspect Ratios for Scanning Probe Microscopy and Other Applications," IEEE Proceedings of Micro Electro Mechanical Systems Conference, pp. 88–93 (1995).

*Laermer, et al., "Bosch Deep Silicon Etching: Improving Uniformity and Etch Rate for Advanced MEMS Applications," *Micro Electro Mechanical Systems,* Orlando, Fl, USA, (Jan. 17–21, 1999).1

Langer, "Drug Delivery and Targeting," *Nature* 392:5–10 (1998).

Lehmann, "Porous Silicon—A New Material for MEMS", IEEE Proceedings of the Micro Electro Mechanical Systems Conference, pp. 1–6 (1996).

Lin, et al., "Silicon Processed Microneedles," The 7th International Conference on Solid–State Sensors and Actuators 237–240 (1993).

Martin, et al., "Template Synthesis of Organic Microtubules," *J. Am. Chem. Soc.* 112:8976–8977 (1990).

Najafi, et al., "Strength Characterization of Silicon Microprobes in Neurophysiological Tissues," *IEEE Transcriptions on Biomedical Engineering* 37(5): 474–481 (1990).

Prausnitz, "Reversible Skin Permeabilization for Transdermal Delivery of Macromolecules," *Critical Reviews in Therapeutic Drug Carrier Systems* 37(5): 474–481 (1990).

*Proceedings of the IEEE MIcro Electro Mechanical Systems Conference 1987–1998; Rai–Choudhury, ed., *Handbook of Microlithography, Micromaching & Microfabrication* (SPIE Optical Engineering Press, Bellingham, WA 1997).

*Quan, "Plasma etch yields microneedle arrays," *Electronic Engineering Times* 63:63–64 (1998).

Reiss, "Glucose– and Blood–Monitoring Systems Vie for Top Spot," *Biophotonics Int'l,* pp. 43–45 (1997).

*Runyan, et al., *Semiconductor Integrated Circuit Processing Technology,* Addison–Wesley Publishing Co.:Reading, MA, 1990.

*Schift, et al., "Fabrication of replicated high precision insert elements for micro–optical bench arrangements" *Proc. SPIE—International Soc. Optical Engineer* 3513:122–134 (1998).

Talbot, et al., "Polymolding: Two Wafer Polysilicon Micromoding of Closed–Flow Passages for Microneedles and Microfluidic Devices," *Solid–State Sensor and Actuator Workshop Hilton Head Island,* South Carolina, Jun. 8–11 266–268 (1988).

Trimmer, et al., "Injection of DNA into Plant and Animal Tissues with Micromechanical Piercing Structures," IEEE Proceedings of Micro Electro Mechanical Systems Conference, pp. 111–15 (1995).

*Weber, et al., "Micromolding—a powerful tool for the large scale production of precise microstructures," *Proc. SPIE—International Soc. Optical Engineer* 2879:156–167 (1996).

Zuska, "Microtechnology Opens Doors to the Universe of Small Space," *Medical Device and Diagnostic Industry,* p. 131 (1997).

* cited by examiner

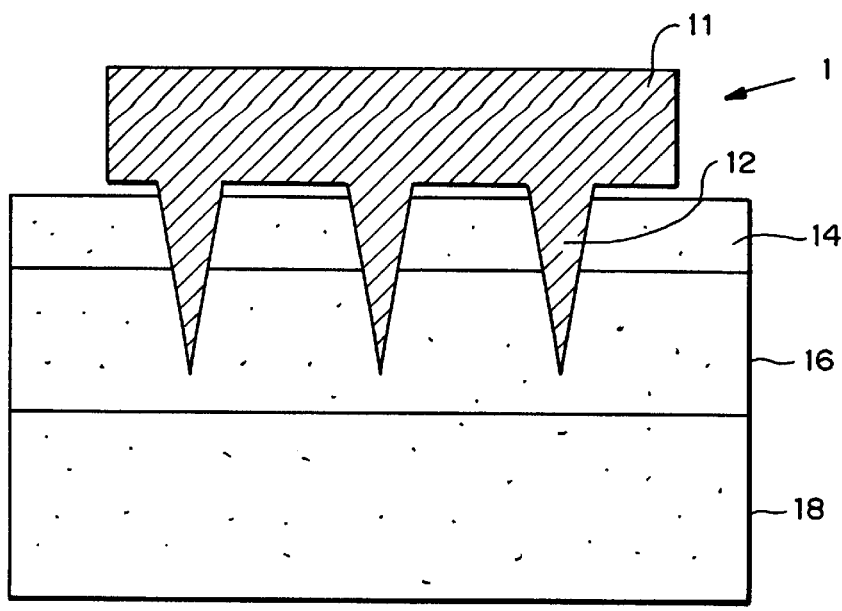
FIG. 1A
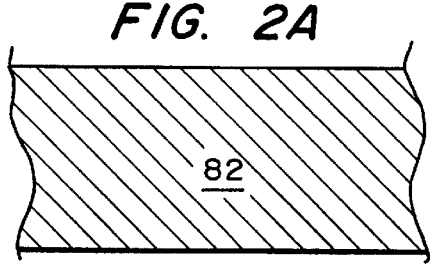
FIG. 2A
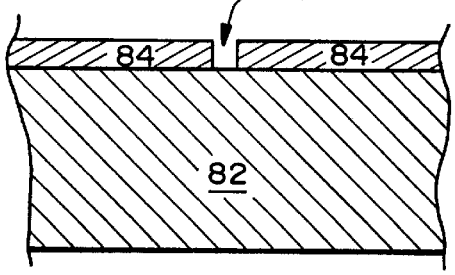
FIG. 2B
FIG. 2C
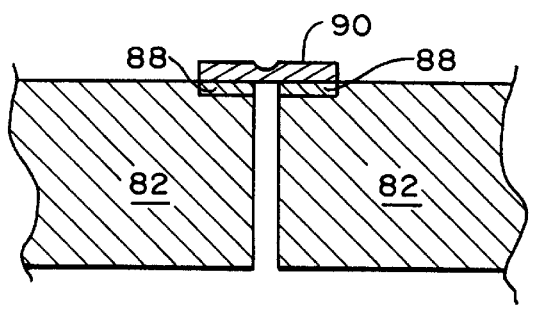
FIG. 2D
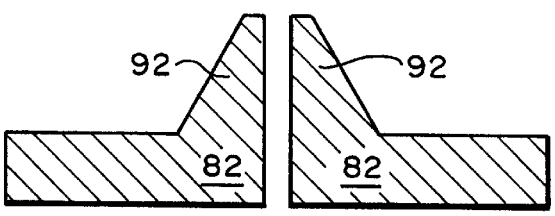
FIG. 2E
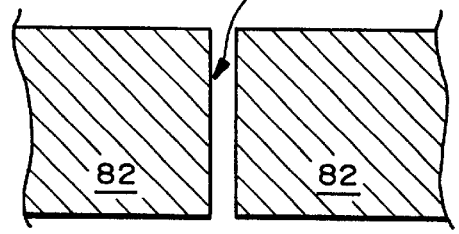

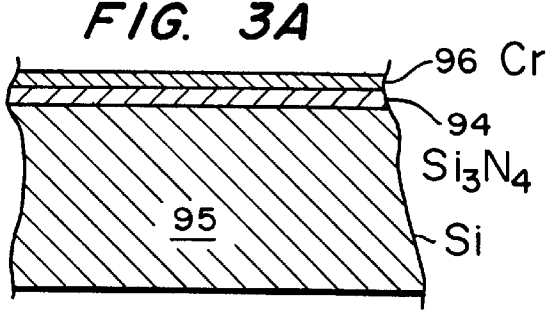
FIG. 3A
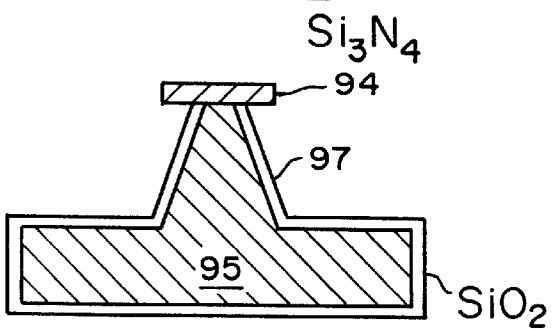
FIG. 3E
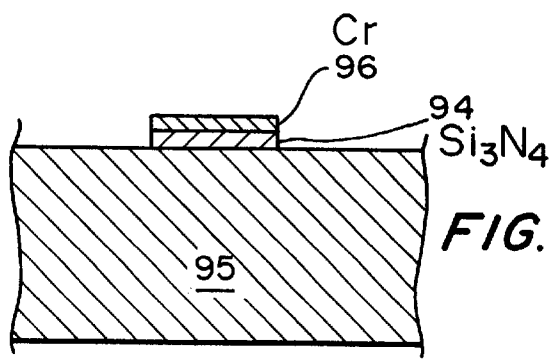
FIG. 3B
FIG. 3C
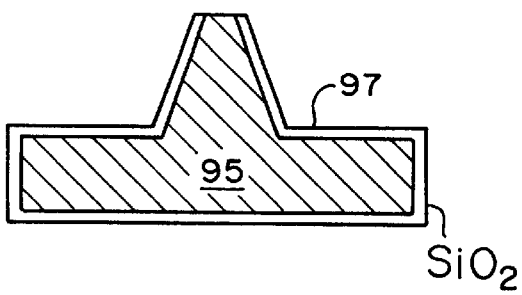
FIG. 3F
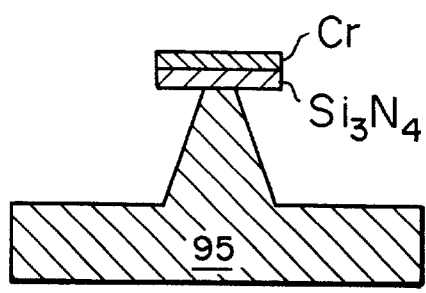
FIG. 3D
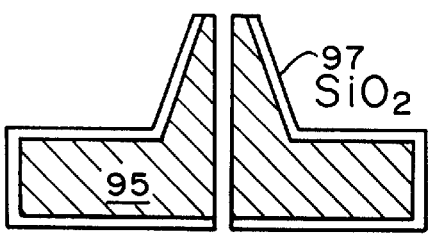
FIG. 3G
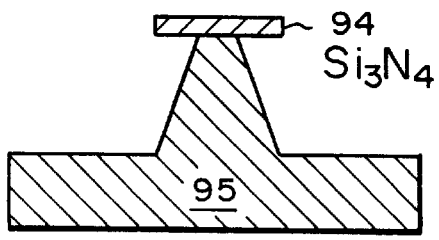

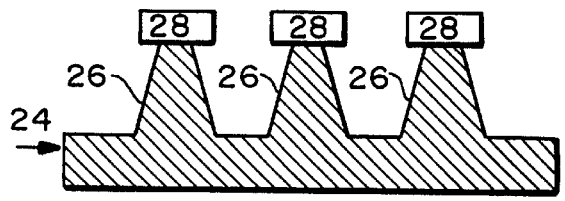
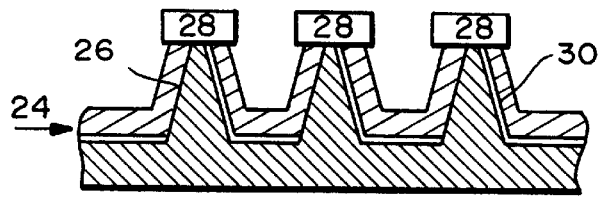
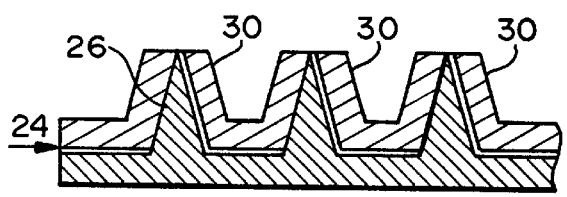
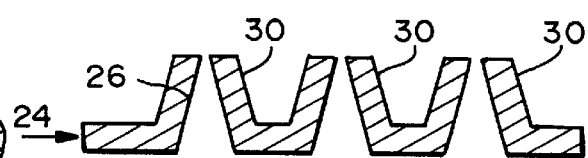
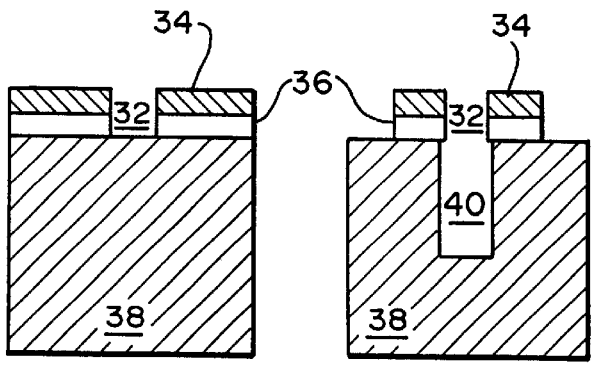
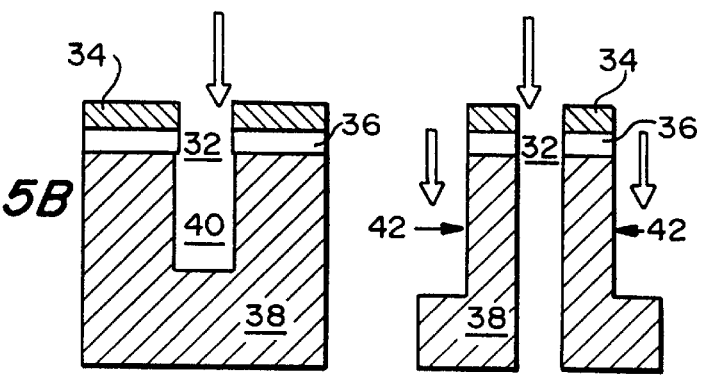

ELECTROPLATED STRUCTURE

MICRONEEDLE DEVICES AND METHODS OF MANUFACTURE AND USE THEREOF

CROSS-REFERENCE TO RELATED APPLICATIONS

This is a continuation-in-part of U.S. Ser. No. 09/095,221, filed Jun. 10, 1998 now U.S. Pat. No. 6,193,700.

STATEMENT REGARDING FEDERALLY SPONSORED RESEARCH

The government has certain rights in this invention by virtue of Grant Number BES-9624832 awarded by the U.S. National Science Foundation to Mark R. Prausnitz, and by virtue of Contract Number DABT63-95-C-0114 awarded by the U.S. Defense Advanced Research Projects Agency (DARPA).

BACKGROUND OF THE INVENTION

This invention is generally in the field of devices for the transport of therapeutic or biological molecules across tissue barriers, such as for drug delivery.

Numerous drugs and therapeutic agents have been developed in the battle against disease and illness. However, a frequent limitation of these drugs is their delivery: how to transport drugs across biological barriers in the body (e.g., the skin, the oral mucosa, the blood-brain barrier), which normally do not transport drugs at rates that are therapeutically useful or optimal.

Drugs are commonly administered orally as pills or capsules. However, many drugs cannot be effectively delivered in this manner, due to degradation in the gastrointestinal tract and/or elimination by the liver. Moreover, some drugs cannot effectively diffuse across the intestinal mucosa. Patient compliance may also be a problem, for example, in therapies requiring that pills be taken at particular intervals over a prolonged time.

Another common technique for delivering drugs across a biological barrier is the use of a needle, such as those used with standard syringes or catheters, to transport drugs across (through) the skin. While effective for this purpose, needles generally cause pain; local damage to the skin at the site of insertion; bleeding, which increases the risk of disease transmission; and a wound sufficiently large to be a site of infection. The withdrawal of bodily fluids, such as for diagnostic purposes, using a conventional needle has these same disadvantages. Needle techniques also generally require administration by one trained in its use. The needle technique also is undesirable for long term, controlled continuous drug delivery.

Similarly, current methods of sampling biological fluids are invasive and suffer from the same disadvantages. For example, needles are not preferred for frequent routine use, such as sampling of a diabetic's blood glucose or delivery of insulin, due to the vascular damage caused by repeated punctures. No alternative methodologies are currently in use. Proposed alternatives to the needle require the use of lasers or heat to create a hole in the skin, which is inconvenient, expensive, or undesirable for repeated use.

An alternative delivery technique is the transdermal patch, which usually relies on diffusion of the drug across the skin. However, this method is not useful for many drugs, due to the poor permeability (i.e. effective barrier properties) of the skin. The rate of diffusion depends in part on the size and hydrophilicity of the drug molecules and the concentration gradient across the stratum corneum. Few drugs have the necessary physiochemical properties to be effectively delivered through the skin by passive diffusion. Iontophoresis, electroporation, ultrasound, and heat (so-called active systems) have been used in an attempt to improve the rate of delivery. While providing varying degrees of enhancement, these techniques are not suitable for all types of drugs, failing to provide the desired level of delivery. In some cases, they are also painful and inconvenient or impractical for continuous controlled drug delivery over a period of hours or days. Attempts have been made to design alternative devices for active transfer of drugs, or analyte to be measured, through the skin.

For example, U.S. Pat. No. 5,879,326 to Godshall et al. and PCT WO 96/37256 by Silicon Microdevices, Inc. disclose a transdermal drug delivery apparatus that includes a cutter portion having a plurality of microprotrusions, which have straight sidewalls, extending from a substrate that is in communication with a drug reservoir. In operation, the microprotrusions penetrate the skin until limited by a stop region of the substrate and then are moved parallel to the skin to create incisions. Because the microprotrusions are dragged across the skin, the device creates a wound sufficiently large to be a site of infection. Channels in the substrate adjacent to the microprotrusions allow drug from the reservoir to flow to the skin near the area disrupted by the microprotrusions. Merely creating a wound, rather than using a needle which conveys drug through an enclosed channel into the site of administration, also creates more variability in dosage.

U.S. Pat. No. 5,250,023 to Lee et al. discloses a transdermal drug delivery device, which includes a plurality of skin needles having a diameter in the range of 50 to 400 μm. The skin needles are supported in a water-swellable polymer substrate through which a drug solution permeates to contact the surface of the skin. An electric current is applied to the device to open the pathways created by the skin needles, following their withdrawal from the skin upon swelling of the polymer substrate.

PCT WO 93/17754 by Gross et al. discloses another transdermal drug delivery device that includes a housing having a liquid drug reservoir and a plurality of tubular elements for transporting liquid drug into the skin. The tubular elements may be in the form of hollow needles having inner diameters of less than 1 mm and an outer diameter of 1.0 mm.

While each of these devices has potential use, there remains a need for better drug delivery devices, which make smaller incisions, deliver drug with greater efficiency (greater drug delivery per quantity applied) and less variability of drug administration, and/or are easier to use.

It is therefore an object of the present invention to provide a microneedle device for relatively painless, controlled, safe, convenient transdermal delivery of a variety of drugs.

It is another object of the present invention to provide a microneedle device for controlled sampling of biological fluids in a minimally-invasive, painless, and convenient manner.

It is still another object of the present invention to provide a hollow microneedle array for use in delivery or sensing of drugs or biological fluids or molecules.

SUMMARY OF THE INVENTION

Microneedle devices for transport of molecules, including drugs and biological molecules, across tissue, and methods for manufacturing the devices, are provided. The microneedle devices permit drug delivery or removal of body fluids at clinically relevant rates across skin or other tissue barriers, with minimal or no damage, pain, or irritation to the tissue. Microneedles can be formed of biodegradable or non-biodegradable polymeric materials or metals. In a preferred embodiment, the microneedles are formed of a biodegradable polymer. In another preferred embodiment, the device includes a means for temporarily securing the microneedle device to the biological barrier to facilitate transport.

Methods are provided for making porous or hollow microneedles. A preferred method for making a microneedle includes forming a micromold having sidewalls which define the outer surface of the microneedle. The micromold can be formed, for example, by photolithographically defining one or more holes in a substrate, or by laser based cutting (either serially or by using lithographic projection), or by using a mold-insert. In a preferred embodiment, the method includes electroplating the sidewalls to form the hollow microneedle, and then removing the micromold from the microneedle.

The microneedle device is useful for delivery of fluid material into or across a biological barrier wherein the fluid material is delivered from one or more chambers in fluid connection with at least one of the microneedles. The device preferably further includes a means for controlling the flow of material through the microneedles. Representative examples of these means include the use of permeable membranes, fracturable impermeable membranes, valves, and pumps, and electrical means.

BRIEF DESCRIPTION OF THE DRAWINGS

FIG. 1a is a side elevational view of a preferred embodiment of the microneedle device inserted into human skin.

FIGS. 2a–e are side cross-sectional views of a method for making microneedles.

FIGS. 3a–g are side cross-sectional views of a method for making a hollow microneedle.

FIGS. 4a through 4d are side cross-sectional views illustrating a preferred method for making hollow microneedles.

FIGS. 5a through 5d are side cross-sectional views illustrating a preferred method for making hollow silicon microtubes.

DETAILED DESCRIPTION OF THE INVENTION

1. Biological Barriers

Figure 1B:
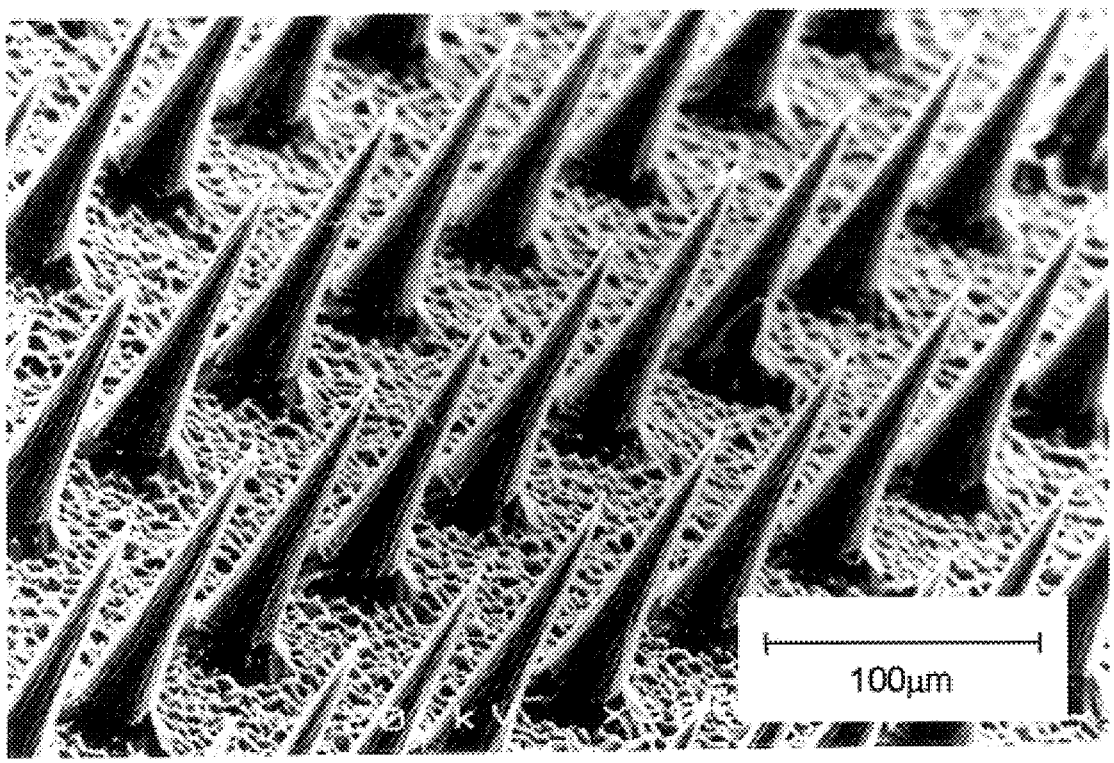
FIG. 1b is a diagram of one embodiment of microneedles.

The devices disclosed herein are useful in transport of material into or across biological barriers including the skin (or parts thereof); the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers can be in humans or other types of animals, as well as in plants, insects, or other organisms, including bacteria, yeast, fungi, and embryos.

The microneedle devices can be applied to tissue internally with the aid of a catheter or laparoscope. For certain applications, such as for drug delivery to an internal tissue, the devices can be surgically implanted.

The microneedle device disclosed herein is typically applied to skin. The stratum corneum is the outer layer, generally between 10 and 50 cells, or between 10 and 20 $\mu$m thick. Unlike other tissue in the body, the stratum corneum contains "cells" (called keratinocytes) filled with bundles of cross-linked keratin and keratohyalin surrounded by an extracellular matrix of lipids. It is this structure that is believed to give skin its barrier properties, which prevents therapeutic transdermal administration of many drugs. Below the stratum corneum is the viable epidermis, which is between 50 and 100 $\mu$m thick. The viable epidermis contains no blood vessels, and it exchanges metabolites by diffusion to and from the dermis. Beneath the viable epidermis is the dermis, which is between 1 and 3 mm thick and contains blood vessels, lymphatics, and nerves.

2. The Microneedle Device

The microneedle devices disclosed herein include a substrate; one or more microneedles; and, optionally, a reservoir for delivery of drugs or collection of analyte, as well as pump(s), sensor(s), and/or microprocessor(s) to control the interaction of the foregoing.

a. Substrate

The substrate of the device can be constructed from a variety of materials, including metals, ceramics, semiconductors, organics, polymers, and composites. The substrate includes the base to which the microneedles are attached or integrally formed. A reservoir may also be attached to the substrate.

b. Microneedle

The microneedles of the device can be constructed from a variety of materials, including metals, ceramics, semiconductors, organics, polymers, and composites. Preferred materials of construction include pharmaceutical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluorethylene (TEFLON™), and polyesters.

Generally, the microneedles should have the mechanical strength to remain intact for delivery of drugs, or serve as a conduit for the collection of biological fluid, while being inserted into the skin, while remaining in place for up to a number of days, and while being removed. In embodiments where the microneedles are formed of biodegradable polymers, however, this mechanical requirement is less stringent, since the microneedles or tips thereof can break off, for example in the skin, and will biodegrade. Nonetheless, even a biodegradable microneedle still needs to remain intact at least long enough for the microneedle to serve its intended purpose (e.g, its conduit function). Therefore, biodegradable microneedles can provide an increased level of safety, as compared to nonbiodegradable ones. The microneedles should be sterilizable using standard methods.

The microneedles can be formed of a porous solid, with or without a sealed coating or exterior portion, or hollow. As used herein, the term "porous" means having pores or voids throughout at least a portion of the microneedle structure, sufficiently large and sufficiently interconnected to permit passage of fluid and/or solid materials through the microneedle. As used herein, the term "hollow" means having one or more substantially annular bores or channels through the interior of the microneedle structure, having a diameter sufficiently large to permit passage of fluid and/or solid materials through the microneedle. The annular bores may extend throughout all or a portion of the needle in the direction of the tip to the base, extending parallel to the direction of the needle or branching or exiting at a side of the needle, as appropriate. A solid or porous microneedle can be hollow. One of skill in the art can select the appropriate porosity and/or bore features required for specific applications. For example, one can adjust the pore size or bore diameter to permit passage of the particular material to be transported through the microneedle device.

The microneedles can have straight or tapered shafts. A hollow microneedle that has a substantially uniform diameter, which needle does not taper to a point, is referred to herein as a "microtube." As used herein, the term "microneedle" includes both microtubes and tapered needles unless otherwise indicated. In a preferred embodiment, the diameter of the microneedle is greatest at the base end of the microneedle and tapers to a point at the end distal the base. The microneedle can also be fabricated to have a shaft that includes both a straight (untapered) portion and a tapered portion.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The shaft can have one or more bores. The cross-sectional dimensions typically are between about 10 nm and 1 mm, preferably between 1 micron and 200 microns, and more preferably between 10 and 100 $\mu$m. The outer diameter is typically between about 10 $\mu$m and about 100 $\mu$m, and the inner diameter is typically between about 3 $\mu$m and about 80 $\mu$m.

The length of the microneedles typically is between about 1 $\mu$m and 1 mm, preferably between 10 microns and 500 microns, and more preferably between 30 and 200 $\mu$m. The length is selected for the particular application, accounting for both an inserted and uninserted portion. An array of microneedles can include a mixture of microneedles having, for example, various lengths, outer diameters, inner diameters, cross-sectional shapes, and spacings between the microneedles.

The microneedles can be oriented perpendicular or at an angle to the substrate. Preferably, the microneedles are oriented perpendicular to the substrate so that a larger density of microneedles per unit area of substrate can be provided. An array of microneedles can include a mixture of microneedle orientations, heights, or other parameters.

In a preferred embodiment of the device, the substrate and/or microneedles, as well as other components, are formed from flexible materials to allow the device to fit the contours of the biological barrier, such as the skin, vessel walls, or the eye, to which the device is applied. A flexible device will facilitate more consistent penetration during use, since penetration can be limited by deviations in the attachment surface. For example, the surface of human skin is not flat due to dermatoglyphics (i.e. tiny wrinkles) and hair.

c. Reservoir

The microneedle device may include a reservoir in communication with the microneedles. The reservoir can be attached to the substrate by any suitable means. In a preferred embodiment, the reservoir is attached to the back of the substrate (opposite the microneedles) around the periphery, using an adhesive agent (e.g., glue). A gasket may also be used to facilitate formation of a fluid-tight seal.

In a preferred embodiment, the reservoir contains drug, for delivery through the microneedles. The reservoir may be a hollow vessel, a porous matrix, or a solid form including drug which is transported therefrom. The reservoir can be formed from a variety of materials that are compatible with the drug or biological fluid contained therein. Preferred materials include natural and synthetic polymers, metals, ceramics, semiconductors, organics, and composites.

The microneedle device can include one or a plurality of chambers for storing materials to be delivered. In the embodiment having multiple chambers, each can be in fluid connection with all or a portion of the microneedles of the device array. In one embodiment, at least two chambers are used to separately contain drug (e.g., a lyophilized drug, such as a vaccine) and an administration vehicle (e.g., saline) in order to prevent or minimize degradation during storage. Immediately before use, the contents of the chambers are mixed. Mixing can be triggered by any means, including, for example, mechanical disruption (i.e. puncturing or breaking), changing the porosity, or electrochemical degradation of the walls or membranes separating the chambers. In another embodiment, a single device is used to deliver different drugs, which are stored separately in different chambers. In this embodiment, the rate of delivery of each drug can be independently controlled.

In a preferred embodiment, the reservoir should be in direct contact with the microneedles and have holes through which drug could exit the reservoir and flow into the interior of hollow or porous microneedles. In another preferred embodiment, the reservoir has holes which permit the drug to transport out of the reservoir and onto the skin surface. From there, drug is transported into the skin, either through hollow or porous microneedles, along the sides of solid microneedles, or through pathways created by microneedles in the skin.

d. Transport Control Components

The microneedle device also must be capable of transporting material across the barrier at a useful rate. For example, the microneedle device must be capable of delivering drug across the skin at a rate sufficient to be therapeutically useful. The device may include a housing with microelectronics and other micromachined structures to control the rate of delivery either according to a preprogrammed schedule or through active interface with the patient, a healthcare professional, or a biosensor. The rate can be controlled by manipulating a variety of factors, including the characteristics of the drug formulation to be delivered (e.g., its viscosity, electric charge, and chemical composition); the dimensions of each microneedle (e.g., its outer diameter and the area of porous or hollow openings);

the number of microneedles in the device; the application of a driving force (e.g., a concentration gradient, a voltage gradient, a pressure gradient); and the use of a valve.

The rate also can be controlled by interposing between the drug in the reservoir and the opening(s) at the base end of the microneedle polymeric or other materials selected for their diffusion characteristics. For example, the material composition and layer thickness can be manipulated using methods known in the art to vary the rate of diffusion of the drug of interest through the material, thereby controlling the rate at which the drug flows from the reservoir through the microneedle and into the tissue.

Transportation of molecules through the microneedles can be controlled or monitored using, for example, various combinations of valves, pumps, sensors, actuators, and microprocessors. These components can be produced using standard manufacturing or microfabrication techniques. Actuators that may be useful with the microneedle devices disclosed herein include micropumps, microvalves, and positioners. In a preferred embodiment, a microprocessor is programmed to control a pump or valve, thereby controlling the rate of delivery.

Flow of molecules through the microneedles can occur based on diffusion, capillary action, or can be induced using conventional mechanical pumps or nonmechanical driving forces, such as electroosmosis or electrophoresis, or convection. For example, in electroosmosis, electrodes are positioned on the biological barrier surface, one or more microneedles, and/or the substrate adjacent the needles, to create a convective flow which carries oppositely charged ionic species and/or neutral molecules toward or into the biological barrier. In a preferred embodiment, the microneedle device is used in combination with another mechanism that enhances the permeability of the biological barrier, for example by increasing cell uptake or membrane disruption, using electric fields, ultrasound, chemical enhancers, viruses, pH, heat and/or light.

Passage of the microneedles, or drug to be transported via the microneedles, can be manipulated by shaping the microneedle surface, or by selection of the material forming th microneedle surface (which could be a coating rather than the microneedle per se). For example, one or more grooves on the outside surface of the microneedles can be used to direct the passage of drug, particularly in a liquid state. Alternatively, the physical surface properties of the microneedle could be manipulated to either promote or inhibit transport of material along the microneedle surface, such as by controlling hydrophilicity or hydrophobicity.

The flow of molecules can be regulated using a wide range of valves or gates. These valves can be the type that are selectively and repeatedly opened and closed, or they can be single-use types. For example, in a disposable, single-use drug delivery device, a fracturable barrier or one-way gate may be installed in the device between the reservoir and the opening of the microneedles. When ready to use, the barrier can be broken or gate opened to permit flow through the microneedles. Other valves or gates used in the microneedle devices can be activated thermally, electrochemically, mechanically, or magnetically to selectively initiate, modulate, or stop the flow of molecules through the needles. In a preferred embodiment, flow is controlled by using a rate-limiting membrane as a "valve."

The microneedle devices can further include a flowmeter or other means to monitor flow through the microneedles and to coordinate use of the pumps and valves.

e. Sensors

Useful sensors may include sensors of pressure, temperature, chemicals, and/or electromagnetic fields. Biosensors can be located on the microneedle surface, inside a hollow or porous microneedle, or inside a device in communication with the body tissue via the microneedle (solid, hollow, or porous). These microneedle biosensors can include four classes of principal transducers: potentiometric, amperometric, optical, and physiochemical. An amperometric sensor monitors currents generated when electrons are exchanged between a biological system and an electrode. Blood glucose sensors frequently are of this type.

The microneedle may function as a conduit for fluids, solutes, electric charge, light, or other materials. In one embodiment, hollow microneedles can be filled with a substance, such as a gel, that has a sensing functionality associated with it. In an application for sensing based on binding to a substrate or reaction mediated by an enzyme, the substrate or enzyme can be immobilized in the needle interior, which would be especially useful in a porous needle to create an integral needle/sensor.

Wave guides can be incorporated into the microneedle device to direct light to a specific location, or for dection, for example, using means such as a pH dye for color evaluation. Similarly, heat, electricity, light or other energy forms may be precisely transmitted to directly stimulate, damage, or heal a specific tissue or intermediary (e.g., tattoo remove for dark skinned persons), or diagnostic purposes, such as measurement of blood glucose based on IR spectra or by chromatographic means, measuring a color change in the presence of immobilized glucose oxidase in combination with an appropriate substrate.

f. Attachment Features

A collar or flange also can be provided with the device, for example, around the periphery of the substrate or the base. It preferably is attached to the device, but alternatively can be formed as integral part of the substrate, for example by forming microneedles only near the center of an "oversized" substrate. The collar can also emanate from other parts of the device. The collar can provide an interface to attach the microneedle array to the rest of the device, and can facilitate handling of the smaller devices.

In a preferred embodiment, the microneedle device includes an adhesive to temporarily secure the device to the surface of the biological barrier. The adhesive can be essentially anywhere on the device to facilitate contact with the biological barrier. For example, the adhesive can be on the surface of the collar (same side as microneedles), on the surface of the substrate between the microneedles (near the base of the microneedles), or a combination thereof.

g. Transdermal Microneedle Device

FIG. 1a is a side elevational view of a schematic of a preferred embodiment of the microneedle device inserted into skin. The device 10 includes an upper portion or substrate 11 from which a plurality of microneedles 12 protrude. The height of the upper portion 11 is between about 1 $\mu$m and 1 cm, and the width of the upper portion is between about 1 mm and 10 cm. The upper portion 11 of the device can be solid or hollow, and may include multiple compartments. In a preferred embodiment for drug delivery, the upper portion 11 contains one or more drugs to be delivered. It is also preferred that the upper portion include one or more sensors and/or an apparatus (e.g., pump or electrode) to drive (provide/direct the force) transport of the drug or other molecules.

The height (or length) of the microneedles 12 generally is between about 1 $\mu$m and 1 mm. The diameter and length both affect pain as well as functional properties of the needles. In transdermal applications, the "insertion depth" of the microneedles 12 is preferably less than about 100 μm, more preferably about 30 μm, so that insertion of the microneedles 12 into the skin through the stratum corneum 14 does not penetrate past the epidermis 16 into the dermis 18 (as described below), thereby avoiding contacting nerves and reducing the potential for causing pain. In such applications, the actual length of the microneedles may be longer, since the portion of the microneedles distal the tip may not be inserted into the skin; the uninserted length depends on the particular device design and configuration. The actual (overall) height or length of microneedles 12 should be equal to the insertion depth plus the uninserted length.

The diameter of each microneedle 12 generally is between about 10 nm and 1 mm, and preferably leaves a residual hole (following microneedle insertion and withdrawal) of less than about 1 μm, to avoid making a hole which would allow bacteria to enter the penetration wound. The actual microneedle diameter should be larger than 1 μm, since the hole likely will contract following withdrawal of the microneedle. The diameter of microneedle 12 more preferably is between about 1 μm and 100 μm. Larger diameter and longer microneedles are acceptable, so long as the microneedle can penetrate the biological barrier to the desired depth and the hole remaining in the skin or other tissue following withdrawal of the microneedle is sufficiently small, preferably small enough to exclude bacterial entry. The microneedles 12 can be solid or porous, and can include one or more bores connected to upper portion 11.

3. Methods of Making Microneedle Devices

The microneedle devices are made by microfabrication processes, by creating small mechanical structures in silicon, metal, polymer, and other materials. These microfabrication processes are based on well-established methods used to make integrated circuits, electronic packages and other microelectronic devices, augmented by additional methods used in the field of micromachining. The microneedle devices can have dimensions as small as a few nanometers and can be mass-produced at low per-unit costs.

a. Microfabrication Processes

Microfabrication processes that may be used in making the microneedles disclosed herein include lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation). See generally Jaeger, *Introduction to Microelectronic Fabrication* (Addison-Wesley Publishing Co., Reading Mass. 1988); Runyan, et al., Semiconductor Integrated Circuit Processing Technology (Addison-Wesley Publishing Co., Reading Mass. 1990); *Proceedings of the IEEE Micro Electro Mechanical Systems Conference* 1987–1998; Rai-Choudhury, ed., *Handbook of Microlithography, Micromachining & Microfabrication* (SPIE Optical Engineering Press, Bellingham, Wash. 1997).

The following methods are preferred for making microneedles.

i. Electrochemical Etching of Silicon

In this method, electrochemical etching of solid silicon to porous silicon is used to create extremely fine (on the order of 0.01 μm) silicon networks which can be used as piercing structures. This method uses electrolytic anodization of silicon in aqueous hydrofluoric acid, potentially in combination with light, to etch channels into the silicon. By varying the doping concentration of the silicon wafer to be etched, the electrolytic potential during etching, the incident light intensity, and the electrolyte concentration, control over the ultimate pore structure can be achieved. The material not etched (i.e. the silicon remaining) forms the microneedles. This method has been used to produce irregular needle-type structures measuring tens of nanometers in width.

ii. Plasma Etching

This process uses deep plasma etching of silicon to create microneedles with diameters on the order of 0.1 μm or larger. Needles are patterned directly using photolithography, rather than indirectly by controlling the voltage (as in electrochemical etching), thus providing greater control over the final microneedle geometry.

In this process, an appropriate masking material (e.g., metal) is deposited onto a silicon wafer substrate and patterned into dots having the diameter of the desired microneedles. The wafer is then subjected to a carefully controlled plasma based on fluorine/oxygen chemistries to etch very deep, high aspect ratio trenches into the silicon. See, e.g., Jansen, et al., "The Black Silicon Method IV: The Fabrication of Three-Dimensional Structures in Silicon with High Aspect Ratios for Scanning Probe Microscopy and Other Applications," *IEEE Proceedings of Micro Electro Mechanical Systems Conference*, pp. 88–93 (1995). Those regions protected by the metal mask remain and form the needles. This method is further described in Example 1 below. FIG. 1b provides a diagram of microneedles fabricated by this method.

iii. Electroplating

In this process, a metal layer is first evaporated onto a planar substrate. A layer of photoresist is then deposited onto the metal to form a patterned mold which leaves an exposed-metal region in the shape of needles. By electroplating onto the exposed regions of the metal seed layer, the mold bounded by photoresist can be filled with electroplated material. Finally, the substrate and photoresist mold are removed, leaving the finished microneedle array. The microneedles produced by this process generally have diameters on the order of 1 μm or larger. See, e.g., Frazier, et al., "Two dimensional metallic microelectrode arrays for extracellular stimulation and recording of neurons", *IEEE Proceedings of the Micro Electro Mechanical Systems Conference*, pp. 195–200 (1993).

iv. Other Processes

Another method for forming microneedles made of silicon or other materials is to use microfabrication techniques such as photolithography, plasma etching, or laser ablation to make a mold form (A), transferring that mold form to other materials using standard mold transfer techniques, such as embossing or injection molding (B), and reproducing the shape of the original mold form (A) using the newly-created mold (B) to yield the final microneedles (C). Alternatively, the creation of the mold form (A) could be skipped and the mold (B) could be microfabricated directly, which could then be used to create the final microneedles (C).

Another method of forming solid silicon microneedles is by using epitaxial growth on silicon substrates, as is utilized by Containerless Research, Inc. (Evanston, Ill., USA) for its products.

b. Hollow or Porous Microneedles

In a preferred embodiment, microneedles are made with pores or other pathways through which material may be transported. The following descriptions outline representative methods for fabricating either porous or hollow microneedles.

i. Porous Microneedles

Rather than having a single, well-defined hole down the length of the needle, porous needles are filled with a network of channels or pores which allow conduction of fluid or energy through the needle shaft. It has been shown that by appropriate electrochemical oxidation of silicon, pore arrays with high aspect ratios and a range of different pore size regimes can be formed; these pore regimes are defined as (1) microporous regime with average pore dimensions less than 2 nm, (2) mesoporous regime with average pore sizes of between 2 nm and 50 nm, and (3) macroporous regime with pores greater than 50 nm. The mesoporous and macroporous regimes are expected to be most useful for drug delivery. Two approaches to porous needles are generally available, either (a) the silicon wafer is first made porous and then etched as described above to form needles or (b) solid microneedles are etched and then rendered porous, for example, by means of electrochemical oxidation, such as by anodization of a silicon substrate in a hydrofluoric acid electrolyte. The size distribution of the etched porous structure is highly dependent on several variables, including doping kind and illumination conditions, as detailed in Lehmann, "Porous Silicon—A New Material for MEMS", *IEEE Proceedings of the Micro Electro Mechanical Systems Conference,* pp. 1–6 (1996). Porous polymer or metallic microneedles can be formed, for example, by micromolding a polymer containing a volatilizable or leachable material, such as a volatile salt, dispersed in the polymer or metal, and then volatilizing or leaching the dispersed material, leaving a porous polymer matrix in the shape of the microneedle.

ii. Hollow Needles

Three-dimensional arrays of hollow microneedles can be fabricated, for example, using combinations of dry etching processes (Laermer, et al., "Bosch Deep Silicon Etching: Improving Uniformity and Etch Rate for Advanced MEMS Applications," *Micro Electro Mechanical Systems,* Orlando, Fla., USA, (Jan. 17–21, 1999); Despont et al., "High-Aspect-Ratio, Ultrathick, Negative-Tone Near-UV Photoresist for MEMS", *Proc. of IEEE 10th Annual International Workshop on MEMS,* Nagoya, Japan, pp. 518–522 (Jan. 26–30, 1997)); micromold creation in lithographically-defined and/or laser ablated polymers and selective sidewall electroplating; or direct micromolding techniques using epoxy mold transfers.

One or more distinct and continuous pathways are created through the interior of microneedles. In a preferred embodiment, the microneedle has a single annular pathway along the center axis of the microneedle. This pathway can be achieved by initially chemically or physically etching the holes in the material and then etching away microneedles around the hole. Alternatively, the microneedles and their holes can be made simultaneously or holes can be etched into existing microneedles. As another option, a microneedle form or mold can be made, then coated, and then etched away, leaving only the outer coating to form a hollow microneedle. Coatings can be formed either by deposition of a film or by oxidation of the silicon microneedles to a specific thickness, followed by removal of the interior silicon. Also, holes from the backside of the wafer to the underside of the hollow needles can be created using a front-to-backside infrared alignment followed by etching from the backside of the wafer.

a. Silicon Microneedles

One method for hollow needle fabrication is to replace the solid mask used in the formation of solid needles by a mask that includes a solid shape with one or more interior regions of the solid shape removed. One example is a "donut-shaped" mask. Using this type of mask, interior regions of the needle are etched simultaneously with their side walls. Due to lateral etching of the inner side walls of the needle, this may not produce sufficiently sharp walls. In that case, two plasma etches may be used, one to form the outer walls of the microneedle (i.e., the 'standard' etch), and one to form the inner hollow core (which is an extremely anisotropic etch, such as in inductively-coupled-plasma "ICP" etch). For example, the ICP etch can be used to form the interior region of the needle followed by a second photolithography step and a standard etch to form the outer walls of the microneedle. FIG. 2a represents a silicon wafer 82 with a patterned photoresist layer 84 on top of the wafer 82. The wafer 82 is anisotropically etched (FIG. 2b) to form a cavity 86 through its entire thickness (FIG. 2c). The wafer 82 is then coated with a chromium layer 88 followed by a second photoresist layer 90 patterned so as to cover the cavity 86 and form a circular mask for subsequent etching (FIG. 2d). The wafer 82 is then etched by a standard etch to form the outer tapered walls 92 of the microneedle (FIG. 2e).

Alternatively, this structure can be achieved by substituting the chromium mask used for the solid microneedles described in Example I by a silicon nitride layer 94 on the silicon substrate 95 covered with chromium 96, deposited as shown in FIG. 3a and patterned as shown in FIG. 3b. Solid microneedles are then etched as described in Example 1 as shown FIG. 3c, the chromium 96 is stripped (FIG. 3d), and the silicon 95 is oxidized to form a thin layer of silicon dioxide 97 on all exposed silicon surfaces (FIG. 3e). The silicon nitride layer 94 prevents oxidation at the needle tip. The silicon nitride 94 is then stripped (FIG. 3f), leaving exposed silicon at the tip of the needle and oxide-covered silicon 97 everywhere else. The needle is then exposed to an ICP plasma which selectively etches the inner sidewalls of the silicon 95 in a highly anisotropic manner to form the interior hole of the needle (FIG. 3g).

Another-method uses the solid silicon needles described previously as 'forms' around which the actual needle structures are deposited. After deposition, the forms are etched away, yielding the hollow structures. Silica needles or metal needles can be formed using different methods. Silica needles can be formed by creating needle structures similar to the ICP needles described above prior to the oxidation described above. The wafers are then oxidized to a controlled thickness, forming a layer on the shaft of the needle form which will eventually become the hollow microneedle. The silicon nitride is then stripped and the silicon core selectively etched away (e.g., in a wet alkaline solution) to form a hollow silica microneedle.

In a preferred embodiment, an array of hollow silicon microtubes is made using deep reactive ion etching combined with a modified black silicon process in a conventional reactive ion etcher, as described in Example 3 below. First, arrays of circular holes are patterned through photoresist into $SiO_2$, such as on a silicon wafer. Then the silicon can be etched using deep reactive ion etching (DRIE) in an inductively coupled plasma (ICP) reactor to etch deep vertical holes. The photoresist was then removed. Next, a second photolithography step patterns the remaining $SiO_2$ layer into circles concentric to the holes, leaving ring shaped oxide masks surrounding the holes. The photoresist is then removed and the silicon wafer again deep silicon etched, such that the holes are etched completely through the wafer (inside the $SiO_2$ ring) and simultaneously the silicon is etched around the $SiO_2$ ring leaving a cylinder.

This latter process can be varied to produce hollow, tapered microneedles. After an array of holes is fabricated as described above, the photoresist and $SiO_2$ layers are replaced with conformal DC sputtered chromium rings. The second ICP etch is replaced with a $SF_6/O_2$ plasma etch in a reactive ion etcher (RIE), which results in positively sloping outer sidewalls. Henry, et al., "Micromachined Needles for the Transdermal Delivery of Drugs," *Micro Electro Mechanical Systems,* Heidelberg, Germany, pp. 494–498 (Jan. 26–29, 1998).

b. Metal Microneedles

Metal needles can be formed by physical vapor deposition of appropriate metal layers on solid needle forms, which can be made of silicon using the techniques described above, or which can be formed using other standard mold techniques such as embossing or injection molding. The metals are selectively removed from the tips of the needles using electropolishing techniques, in which an applied anodic potential in an electrolytic solution will cause dissolution of metals more rapidly at sharp points, due to concentration of electric field lines at the sharp points. Once the underlying silicon needle forms have been exposed at the tips, the silicon is selectively etched away to form hollow metallic needle structures. This process could also be used to make hollow needles made from other materials by depositing a material other than metal on the needle forms and following the procedure described above.

A preferred method of fabricating hollow metal microneedles utilizes micromold plating techniques, for example which are described as follows and in Examples 4 and 5. In a method for making metal microtubes, which does not require dry silicon etching, a photo-defined mold first is first produced, for example, by spin casting a thick layer, typically 150 μm, of an epoxy (e.g., SU-8) onto a substrate that has been coated with a thin sacrificial layer, typically about 10 to 50 nm. Arrays of cylindrical holes are then photolithographically defined through the epoxy layer, which typically is about 150 μm thick. (Despont, et al., "High-Aspect-Ratio, Ultrathick, Negative-Tone Near-UV Photoresist for MEMS," *Proc. of IEEE $10^{th}$ Annual International Workshop on MEMS,* Nagoya, Japan, pp. 518–522 (Jan. 26–30, 1997)). The diameter of these cylindrical holes defines the outer diameter of the tubes. The upper surface of the substrate, the sacrificial layer, is then partially removed at the bottom of the cylindrical holes in the photoresist. The exact method chosen depends on the choice of substrate. For example, the process has been successfully performed on silicon and glass substrates (in which the upper surface is etched using isotropic wet or dry etching techniques) and copper-clad printed wiring board substrates. In the latter case, the copper laminate is selectively removed using wet etching. Then a seed layer, such as Ti/Cu/Ti (e.g., 30 nm/200 nm/30 nm), is conformally DC sputter-deposited onto the upper surface of the epoxy mold and onto the sidewalls of the cylindrical holes. The seed layer should be electrically isolated from the substrate. Subsequently, one or more electroplatable metals or alloys, such as Ni, NiFe, Au, Cu, or Ti are electroplated onto the seed layer. The surrounding epoxy is then removed, leaving microtubes which each have an interior annular hole that extends through the base metal supporting the tubes. The rate and duration of electroplating is controlled in order to define the wall thickness and inner diameter of the microtubes. In one embodiment, this method was used to produce microtubes having a height of between about 150 and 250 μm, an outer diameter of between about 40 and 120 μm, and an inner diameter of between about 30 and 110 μm (i.e., having a wall thickness of 10 μm). In a typical array, the microtubes have a tube center-to-center spacing of about 150 μm, but can vary depending on the desired needle density.

A variation of this method is preferred for forming tapered microneedles. As described above, photolithography yields holes in the epoxy which have vertical sidewalls, such that the resulting shafts of the microneedles are straight, not tapered. This vertical sidewall limitation can be overcome by molding a preexisting 3D structure, i.e., a mold-insert. The subsequent removal of the mold-insert leaves a mold which can be surface plated similarly to the holes produced by photolithography described above.

Alternatively, non-vertical sidewalls can be produced directly in the polymeric mold into which electroplating will take place. For example, conventional photoresists known in the art can be exposed and developed in such as way as to have the surface immediately adjacent to the mask be wider than the other surface. Specialized greyscale photoresists in combination with greyscale masks can accomplish the same effect. Laser-ablated molds can also be made with tapered sidewalls, e.g., by optical adjustment of the beam (in the case of serial hole fabrication) or of the reticle or mold during ablation (in the case of projection ablation).

To form hollow tapered microneedles, the mold-insert is an array of solid silicon microneedles, formed as described in Henry, et al., "Micromachined Needles for the Transdermal Delivery of Drugs," *Micro Electro Mechanical Systems, Heidelberg, Germany, Jan.* 26–29, pp. 494–498 (1998). First, a layer of a material, such as an epoxy (e.g., SU-8), is spin cast onto the array of silicon microneedles to completely blanket the entire array. The epoxy settles during pre-bake to create a planar surface above the silicon needle tips; the material is then fully pre-baked, photolithographically cross-linked, and post-baked.

The upper surface of the epoxy is then etched away, for example with an $O_2/CHF_3$ plasma, until the needle tips are exposed, preferably leaving between about 1 and 5 μm of tip protruding from the epoxy. The silicon is then selectively removed, for example by using a $SF_6$ plasma or a $HNO_3/HF$ solution. The remaining epoxy micromold is the negative of the microneedles and has a small diameter hole where the tip of the microneedle formerly protruded.

After the removal of the silicon, a seed layer, such as Ti—Cu—Ti is conformally sputter-deposited onto the epoxy micromold. Following the same process sequence described for hollow metal microtubes, one or more electroplatable metals or alloys, such as Ni, NiFe, Au, or Cu, are electroplated onto the seed layer. Finally, the epoxy is removed, for example by using an $O_2/CHF_3$ plasma, leaving an array of hollow metal microneedles. In a preferred embodiment, this method is used to produce microneedles having a height of between about 150 and 250 μm, an outer diameter of between about 40 and 120 μm, and an inner diameter of between about 50 and 100 μm. In a typical array, the microtubes have a tube center-to-center spacing of about 150 μm, but can vary depending on the desired needle density. The microneedles are 150 μm in height with a base diameter of 80 μm, a tip diameter of 10 μm, and a needle to needle spacing of 150 μm.

c. Silicon Dioxide Microneedles

Hollow microneedles formed of silicon dioxide can be made by oxidizing the surface of the silicon microneedle forms (as described above), rather than depositing a metal and then etching away the solid needle forms to leave the hollow silicon dioxide structures. This method is illustrated in FIGS. 4a–4d. FIG. 4a shows an array 24 of needle forms 26 with masks 28 on their tips. In FIG. 4b, the needle forms 26 have been coated with a layer 30 of metal, silicon dioxide or other material. FIG. 4c shows the coated needle forms 26 with the masks 28 removed. Finally, in FIG. 4d, the needle forms 26 have been etched away, leaving hollow needles 30 made of metal, silicon dioxide, or other materials.

In one embodiment, hollow, porous, or solid microneedles are provided with longitudinal grooves or other modifications to the exterior surface of the microneedles. Grooves, for example, should be useful in directing the flow of molecules along the outside of microneedles.

d. Polymer Microneedles

In a preferred method, polymeric microneedles are made using microfabricated molds. For example, the epoxy molds can be made as described above and injection molding techniques can be applied to form the microneedles in the molds (Weber, et al., "Micromolding—a powerful tool for the large scale production of precise microstructures", Proc. SPIE—International Soc. Optical Engineer. 2879, 156–167 (1996); Schift, et al., "Fabrication of replicated high precision insert elements for micro-optical bench arrangements" Proc. SPIE— International Soc. Optical Engineer. 3513, 122–134 (1998). These micromolding techniques are preferred over other techniques described herein, since they can provide relatively less expensive replication, i.e. lower cost of mass production. In a preferred embodiment, the polymer is biodegradable.

4. Microneedle Device Applications

The device may be used for single or multiple uses for rapid transport across a biological barrier or may be left in place for longer times (e.g., hours or days) for long-term transport of molecules. Depending on the dimensions of the device, the application site, and the route in which the device is introduced into (or onto) the biological barrier, the device may be used to introduce or remove molecules at specific locations.

As discussed above, FIG. 1 shows a side elevational view of a schematic of a preferred embodiment of the microneedle device 10 in a transdermal application. The device 10 is applied to the skin such that the microneedles 12 penetrate through the stratum corneum and enter the viable epidermis so that the tip of the microneedle at least penetrates into the viable epidermis. In a preferred embodiment, drug molecules in a reservoir within the upper portion 11 flow through or around the microneedles and into the viable epidermis, where the drug molecules then diffuse into the dermis for local treatment or for transport through the body.

To control the transport of material out of or into the device through the microneedles, a variety of forces or mechanisms can be employed. These include pressure gradients, concentration gradients, electricity, ultrasound, receptor binding, heat, chemicals, and chemical reactions. Mechanical or other gates in conjunction with the forces and mechanisms described above can be used to selectively control transport of the material.

In particular embodiments, the device should be "user-friendly." For example, in some transdermal applications, affixing the device to the skin should be relatively simple, and not require special skills. This embodiment of a microneedle may include an array of microneedles attached to a housing containing drug in an internal reservoir, wherein the housing has a bioadhesive coating around the microneedles. The patient can remove a peel-away backing to expose an adhesive coating, and then press the device onto a clean part of the skin, leaving it to administer drug over the course of, for example, several days.

a. Drug Delivery

Essentially any drug or other bioactive agents can be delivered using these devices. Drugs can be proteins, enzymes, polysaccharides, polynucleotide molecules, and synthetic organic and inorganic compounds. A preferred drug is insulin. Representative agents include anti-infectives, hormones, growth regulators, drugs regulating cardiac action or blood flow, and drugs for pain control. The drug can be for local treatment or for regional or systemic therapy. The following are representative examples, and disorders they are used to treat:

Calcitonin, osteoporosis
Enoxaprin, anticoagulant
Etanercept, rheumatoid arthritis
Erythropoietin, anemia
Fentanyl, postoperative and chronic pain
Filgrastin, low white blood cells from chemotherapy
Heparin, anticoagulant
Insulin, human, diabetes
Interferon Beta I a, multiple sclerosis
Lidocaine, local anesthesia
Somatropin, growth hormone
Sumatriptan, migraine headaches In this way, many drugs can be delivered at a variety of therapeutic rates. The rate can be controlled by varying a number of design factors, including the outer diameter of the microneedle, the number and size of pores or channels in each microneedle, the number of microneedles in an array, the magnitude and frequency of application of the force driving the drug through the microneedle and/or the holes created by the microneedles. For example, devices designed to deliver drug at different rates might have more microneedles for more rapid delivery and fewer microneedles for less rapid delivery. As another example, a device designed to deliver drug at a variable rate could vary the driving force (e.g., pressure gradient controlled by a pump) for transport according to a schedule which was pre-programmed or controlled by, for example, the user or his doctor. The devices can be affixed to the skin or other tissue to deliver drugs continuously or intermittently, for durations ranging from a few seconds to several hours or days.

One of skill in the art can measure the rate of drug delivery for particular microneedle devices using in vitro and in vivo methods known in the art. For example, to measure the rate of transdermal drug delivery, human cadaver skin mounted on standard diffusion chambers can be used to predict actual rates. See Hadgraft & Guy, eds., *Transdermal Drug Delivery: Developmental Issues and Research Initiatives* (Marcel Dekker, New York 1989); Bronaugh & Maibach, *Percutaneous Absorption, Mechanisms—Methodology—Drug Delivery* (Marcel Dekker, New York 1989). After filling the compartment on the dermis side of the diffusion chamber with saline, a microneedle array is inserted into the stratum corneum; a drug solution is placed in the reservoir of the microneedle device; and samples of the saline solution are taken over time and assayed to determine the rates of drug transport.

In an alternate embodiment, biodegradable or non-biodegradable microneedles can be used as the entire drug delivery device, where biodegradable microneedles are a preferred embodiment. For example, the microneedles may be formed of a biodegradable polymer containing a dispersion of an active agent for local or systemic delivery. The agent could be released over time, according to a profile determined by the composition and geometry of the microneedles, the concentration of the drug and other factors. In this way, the drug reservoir is within the matrix of one or more of the microneedles.

In another alternate embodiment, these microneedles may be purposefully sheared off from the substrate after penetrating the biological barrier. In this way, a portion of the microneedles would remain within or on the other side of the biological barrier and a portion of the microneedles and their substrate would be removed from the biological barrier. In the case of skin, this could involve inserting an array into the skin, manually or otherwise breaking off the microneedles tips and then remove the base of the microneedles. The portion of the microneedles which remains in the skin or in or across another biological barrier could then release drug over time according to a profile determined by the composition and geometry of the microneedles, the concentration of the drug and other factors. In a preferred embodiment, the microneedles are made of a biodegradable polymer. The release of drug from the biodegradable microneedle tips could be controlled by the rate of polymer degradation. Microneedle tips could release drugs for local or systemic effect, but could also release other agents, such as perfume, insect repellent and sun block.

Microneedle shape and content could be designed to control the breakage of microneedles. For example, a notch could be introduced into microneedles either at the time of fabrication or as a subsequent step. In this way, microneedles would preferentially break at the site of the notch. Moreover, the size and shape of the portion of microneedles which break off could be controlled not only for specific drug release patterns, but also for specific interactions with cells in the body. For example, objects of a few microns in size are known to be taken up by macrophages. The portions of microneedles that break off could be controlled to be bigger or smaller than that to prevent uptake by macrophages or could be that size to promote uptake by macrophages, which could be desirable for delivery of vaccines.

b. Diagnostic Sensing of Body Fluids (Biosensors)

One embodiment of the devices described herein may be used to remove material from the body across a biological barrier, i.e. for minimally invasive diagnostic sensing. For example, fluids can be transported from interstitial fluid in a tissue into a reservoir in the upper portion of the device. The fluid can then be assayed while in the reservoir or the fluid can be removed from the reservoir to be assayed, for diagnostic or other purposes. For example, interstitial fluids can be removed from the epidermis across the stratum corneum to assay for glucose concentration, which should be useful in aiding diabetics in determining their required insulin dose. Other substances or properties that would be desirable to detect include lactate (important for athletes), oxygen, pH, alcohol, tobacco metabolites, and illegal drugs (important for both medical diagnosis and law enforcement).

The sensing device can be in or attached to one or more microneedles, or in a housing adapted to the substrate. Sensing information or signals can be transferred optically (e.g., refractive index) or electrically (e.g., measuring changes in electrical impedance, resistance, current, voltage, or combination thereof). For example, it may be useful to measure a change as a function of change in resistance of tissue to an electrical current or voltage, or a change in response to channel binding or other criteria (such as an optical change) wherein different resistances are calibrated to signal that more or less flow of drug is needed, or that delivery has been completed.

In one embodiment, one or more microneedle devices can be used for (1) withdrawal of interstitial fluid, (2) assay of the fluid, and/or (3) delivery of the appropriate amount of a therapeutic agent based on the results of the assay, either automatically or with human intervention. For example, a sensor delivery system may be combined to form, for example, a system which withdraws bodily fluid, measures its glucose content, and delivers an appropriate amount of insulin. The sensing or delivery step also can be performed using conventional techniques, which would be integrated into use of the microneedle device. For example, the microneedle device could be used to withdraw and assay glucose, and a conventional syringe and needle used to administer the insulin, or vice versa.

In an alternate embodiment, microneedles may be purposefully sheared off from the substrate after penetrating the biological barrier, as described above. The portion of the microneedles which remain within or on the other side of the biological barrier could contain one or more biosensors. For example, the sensor could change color as its output. For microneedles sheared off in the skin, this color change could be observed through the skin by visual inspection or with the aid of an optical apparatus.

Other than transport of drugs and biological molecules, the microneedles may be used to transmit or transfer other materials and energy forms, such as light, electricity, heat, or pressure. The microneedles, for example, could be used to direct light to specific locations within the body, in order that the light can directly act on a tissue or on an intermediary, such as light-sensitive molecules in photodynamic therapy. The microneedles can also be used for aerosolization or delivery for example directly to a mucosal surface in the nasal or buccal regions or to the pulmonary system.

The microneedle devices disclosed herein also should be useful for controlling transport across tissues other than skin. For example, microneedles could be inserted into the eye across, for example, conjunctiva, sclera, and/or cornea, to facilitate delivery of drugs into the eye. Similarly, microneedles inserted into the eye could facilitate transport of fluid out of the eye, which may be of benefit for treatment of glaucoma. Microneedles may also be inserted into the buccal (oral), nasal, vaginal, or other accessible mucosa to facilitate transport into, out of, or across those tissues. For example, a drug may be delivered across the buccal mucosa for local treatment in the mouth or for systemic uptake and delivery. As another example, microneedle devices may be used internally within the body on, for example, the lining of the gastrointestinal tract to facilitate uptake of orally-ingested drugs or the lining of blood vessels to facilitate penetration of drugs into the vessel wall. For example, cardiovascular applications include using microneedle devices to facilitate vessel distension or immobilization, similarly to a stent, wherein the microneedles/substrate can function as a "staple-like" device to penetrate into different tissue segments and hold their relative positions for a period of time to permit tissue regeneration. This application would be particularly useful with biodegradable devices. These uses may involve invasive procedures to introduce the microneedle devices into the body or could involve swallowing, inhaling, injecting or otherwise introducing the devices in a non-invasive or minimally-invasive manner.

The present invention will be further understood with reference to the following non-limiting examples.

EXAMPLE 1
Fabrication of Solid Silicon Microneedles

A chromium masking material was deposited onto silicon wafers and patterned into dots having a diameter approximately equal to the base of the desired microneedles. The wafers were then loaded into a reactive ion etcher and subjected to a carefully controlled plasma based on fluorine/oxygen chemistries to etch very deep, high aspect ratio valleys into the silicon. Those regions protected by the metal mask remain and form the microneedles.

<100>-oriented, prime grade, 450–550 $\mu$m thick, 10–15 Ω-cm silicon wafers (Nova Electronic Materials Inc., Richardson, Tex.) were used as the starting material. The wafers were cleaned in a solution of 5 parts by volume deionized water, 1 part 30% hydrogen peroxide, and I part 30% ammonium hydroxide (J. T. Baker, Phillipsburg, N.J.) at approximately 80° C. for 15 minutes, and then dried in an oven (Blue M Electric, Watertown, Wis.) at 150° C. for 10 minutes. Approximately 1000 Å of chromium (Mat-Vac Technology, Flagler Beach, Fla.) was deposited onto the wafers using a DC-sputterer (601 Sputtering System, CVC Products, Rochester, N.Y.). The chromium layer was patterned into 20 by 20 arrays of 80 $\mu$m diameter dots with 150 $\mu$m center-to-center spacing using the lithographic process described below.

A layer of photosensitive material (1827 photoresist, Shipley, Marlborough, Mass.) was deposited onto the chromium layer covering the silicon wafers. A standard lithographic mask (Telic, Santa Monica, Calif.) bearing the appropriate dot array pattern was positioned on top of the photoresist layer. The wafer and photoresist were then exposed to ultraviolet (UV) light through the mask by means of an optical mask aligner (Hybralign Series 500, Optical Associates, Inc., Milpitas, Calif.). The exposed photoresist was removed by soaking the wafers in a liquid developer (354 developer, Shipley, Marlborough, Mass.) leaving the desired dot array of photoresist on the chromium layer. Subsequently, the wafers were dipped into a chromium etchant (CR-75; Cyanteck Fremont, Calif.), which etched the chromium that had been exposed during the photolithography step, leaving dot arrays of chromium (covered with photoresist) on the surface of the silicon wafer. The photoresist still present on the chromium dots formed the masks needed for fabrication of the microneedles, described below.

The microneedles were fabricated using a reactive ion etching techniques based on the Black Silicon Method developed at the University of Twente. The patterned wafers were etched in a reactive ion etcher (700 series wafer/batch Plasma Processing System, Plasma Therm, St. Petersburg, Fla.) with means for ensuring good thermal contact between the wafers and the underlying platen (Apiezon N, K. J. Lesker, Clairton, Pa.). The wafers were etched using the following gases and conditions: $SF_6$ (20 standard cubic centimeters per minute) and $O_2$ (15 standard cubic centimeters per minute) at a pressure of 150 mTorr and a power of 150 W for a run time of approximately 250 minutes. These conditions caused both deep vertical etching and slight lateral underetching. By controlling the ratio of flow rates of the $SF_6$ and $O_2$ gases used to form the plasma, the aspect ratio of the microneedles could be adjusted. The regions protected by the chromium masks remained and formed the microneedles. Etching was allowed to proceed until the masks fell off due to underetching, resulting in an array of sharp silicon spikes.

EXAMPLE 2
Transdermal Transport Using Solid Microneedles

To determine if microfabricated microneedles could be used to enhance transdermal drug delivery, arrays of microneedles were made using a deep plasma etching technique. Their ability to penetrate human skin without breaking was tested and the resulting changes in transdermal transport were measured.

Arrays of microneedles were fabricated having extremely sharp tips (radius of curvature less than 1 $\mu$m), and are approximately 150 $\mu$m long. Because the skin surface is not flat due to dermatoglyphics and hair, the full length of these microneedles will not penetrate the skin. All experiments were performed at room temperature (23±2° C).

The ability of the microneedles to pierce skin without breaking was then tested. Insertion of the arrays into skin required only gentle pushing. Inspection by light and electron microscopy showed that more than 95% of microneedles within an array pierced across the stratum corneum of the epidermis samples. Moreover, essentially all of the microneedles that penetrated the epidermis remained intact. On those very few which broke, only the top 5–10 $\mu$m was damaged. Microneedle arrays could also be removed without difficulty or additional damage, as well as re-inserted into skin multiple times.

To quantitatively assess the ability of microneedles to increase transdermal transport, calcein permeability of human epidermis with and without inserted microneedle arrays was measured. Calcein crosses skin very poorly under normal circumstances and therefore represents an especially difficult compound to deliver. As expected, passive permeability of calcein across unaltered skin was very low, indicating that the epidermis samples were intact.

Insertion of microneedles into skin was capable of dramatically increasing permeability to calcein. When microneedles were inserted and left embedded in the skin, calcein permeability was increased by more than 1000-fold. Insertion of microneedles for 10 s, followed by their removal, yielded an almost 10,000-fold increase. Finally, insertion of a microneedle array for 1 h, followed by its removal, increased skin permeability by about 25,000-fold. Permeabilities for skin with microneedles inserted and then removed are higher than for skin with microneedles remaining embedded probably because the microneedles themselves or the silicon plate supporting the array may block access to the microscopic holes created in the skin. Light microscopy showed that the holes which remained in the skin after microneedles were removed were approximately 1 $\mu$m in size.

To confirm in vitro experiments which showed that skin permeability can be significantly increased by microneedles, studies were conducted with human volunteers. They indicated that microneedles could be easily inserted into the skin of the forearm or hand. Moreover, insertion of microneedle arrays was never reported to be painful, but sometimes elicited a mild "wearing" sensation described as a weak pressure or the feeling of a piece of tape affixed to the skin. Although transport experiments were not performed in vivo, skin electrical resistance was measured before and after microneedle insertion. Microneedles caused a 50-fold drop in skin resistance, a drop similar to that caused by the insertion of a 30-gauge "macroneedle." Inspection of the site immediately after microneedle insertion showed no holes visible by light microscopy. No erythema, edema or other reaction to microneedles was observed over the hours and days which followed. This indicates that microneedle arrays can permeabilize skin in human subjects in a non-painful and safe manner.

EXAMPLE 3
Fabrication of Silicon Microtubes

Three-dimensional arrays of microtubes were fabricated from silicon, using deep reactive ion etching combined with a modified black silicon process in a conventional reactive ion etcher. The fabrication process is illustrated in FIGS. 5a–d. First, arrays of 40 μm diameter circular holes 32 were patterned through photoresist 34 into a 1 μm thick $SiO_2$ layer 36 on a two inch silicon wafer 38 (FIG. 5a). The wafer 38 was then etched using deep reactive ion etching (DRIE) (Laermer, et al., "Bosch Deep Silicon Etching: Improving Uniformity and Etch Rate for Advanced MEMS Applications," *Micro Electro Mechaiical Systems,* Orlando, Fla., USA (Jan. 17–21, 1999)). in an inductively coupled plasma (ICP) reactor to etch deep vertical holes 40. The deep silicon etch was stopped after the holes 40 are approximately 200 μm deep into the silicon substrate 38 (FIG. 5b) and the photoresist 34 was removed. A second photolithography step patterned the remaining $SiO_2$ layer 36 into circles concentric to the holes, thus leaving ring shaped oxide masks 34 surrounding the holes (FIG. 5c). The photoresist 34 was then removed and the wafer 38 was again deep silicon etched, while simultaneously the holes 40 were etched completely through the wafer 38 (inside the $SiO_2$ ring) and the silicon was etched around the $Sio_2$ ring 38 leaving a cylinder 42 (FIG. 5d). The resulting tubes were 150 μm in height, with an outer diameter of 80 μm, an inner diameter of 40 μm, and a tube center-to-center spacing of 300 μm.

EXAMPLE 4
Micromold Fabrication of Metal Microtubes

Figure 6A:
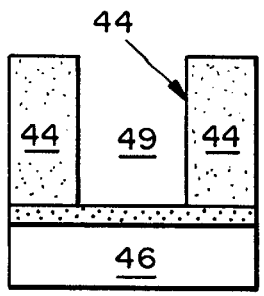
FIGS. 6a through 6e are side cross-sectional views illustrating a preferred method for making hollow metal microtubes.
Figure 6C:
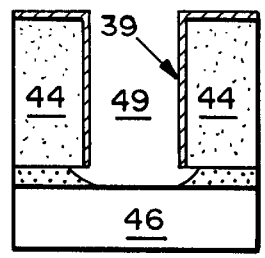
Figure 6B:
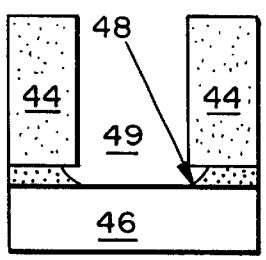
Figure 6D:
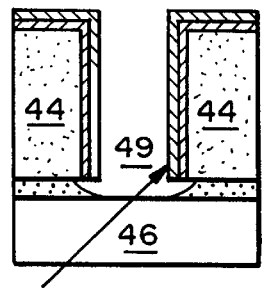
Figure 6E:
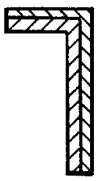

Hollow metal microtubes were prepared without dry silicon etching, using a thick, photo-defined mold of epoxy. The sequences are illustrated in FIGS. 6a–e. First, a thick layer of SU-8 epoxy 44 was spin cast onto a silicon or glass substrate 46 that had been coated with 30 nm of titanium 48, the sacrificial layer. Arrays of cylindrical holes 49 were then photolithographically defined through an epoxy layer 44, typically 150 μm thick (FIG. 6a). The sacrificial layer then was partially removed using a wet etching solution containing hydrofluoric acid and water at the bottom of the cylindrical holes in the SU-8 photoresist 46 (FIG. 6b). A seed layer of Ti/Cu/Ti (30 nm/200 nm/30 nm) 39 was then conformally DC sputter-deposited onto the upper surface of the epoxy mold and onto the sidewalls of the cylindrical holes 49 (FIG. 6c). As shown in FIG. 6c, the seed layer 39 was electrically isolated from the substrate. Subsequently, NiFe was electroplated onto the seed layer 39 (FIG. 6d), the epoxy 44 was removed from the substrate, and the surrounding epoxy 44 was removed (FIG. 6e). The resulting microtubes are 200 μm in height with an outer diameter of 80 lm, an inner diameter of 60 μm, and a tube center-to-center spacing of 150 μm. The holes in the interior of the microtubes protrude through the base metal supporting the tubes.

EXAMPLE 5
Micromold Fabrication of Tapered Microneedles

A micromold having tapered walls was fabricated by molding a preexisting 3-D array of microneedles, i.e. the mold-insert, and subsequently removing the mold insert. The micromold was then surface plated in a manner similar to that for the microtubes described in Example 4. The fabrication sequence is illustrated in FIGS. 7a–7d.

Figure 7A:
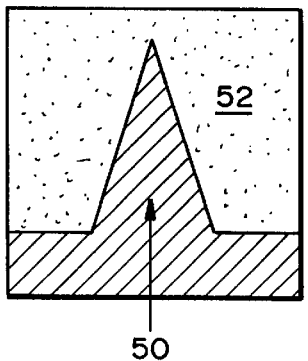
FIGS. 7a through 7d are side cross-sectional views illustrating a preferred method for making tapered metal microneedles.

First, an array of solid silicon microneedles 50 were prepared as described in Henry, et al., "Micromachined Needles for the Transdermal Delivery of Drugs," *Micro Electro Mechanical Systems,* Heidelberg, Germany, Jan. 26–29, pp. 494–498 (1998). Then, a layer of epoxy 52 (SU-8) was spin cast onto the microneedle array to completely blanket the array (FIG. 7a). The epoxy 52 settled during pre-bake to create a planar surface above the tips of the microneedles 50. The epoxy 52 was then fully pre-baked, photolithographically cross-linked, and post-baked.

Figure 7C:
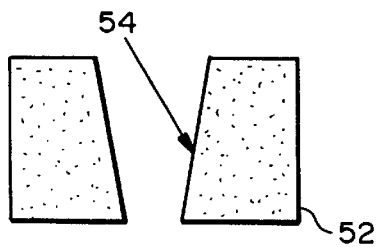
Figure 7B:
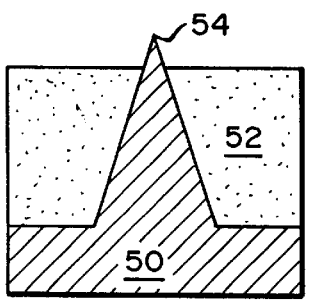
Figure 7D:
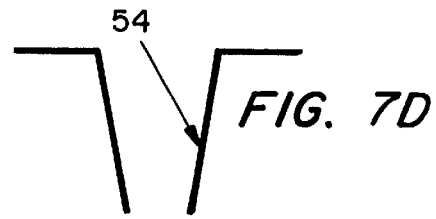

Then, the upper surface of the epoxy 52 was etched away using an $O_2/CHF_3$ plasma until approximately 1 to 2 μm of the needle tips 54 were exposed, protruding from the epoxy 52 (FIG. 7b). The silicon was then selectively removed by using a $SF_6$ plasma (FIG. 7c). The remaining epoxy mold 52 provided a negative of the microneedles with a small diameter hole where the tip of the silicon needle protruded. After the removal of the silicon, a seed layer of Ti—Cu—Ti 54 was conformally sputter-deposited onto the top and sidewalls of the epoxy micromold 52. Following the same process sequence as described in Example 4, NiFe was then electroplated onto the seed layer 54 (FIG. 7c). Finally, the epoxy was removed using an $O_2/CHF_3$ plasma, leaving a 20×20 array of NiFe hollow metal microneedles 54 (FIG. 7d). The microneedles 54 were 150 μm in height with a base diameter of 80 μm, a tip diameter of 10 μm, and a needle to needle spacing of 150 μm.

Figure 8A:
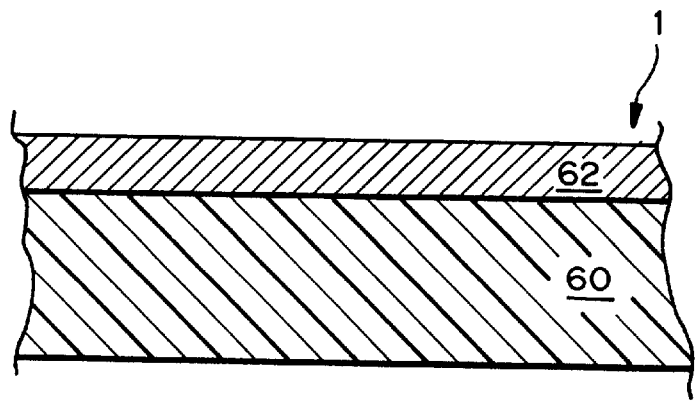
FIGS. 8a through 8d are side cross-sectional views illustrating a method for making tapered microneedles using laser-formed molds.
Figure 8B:
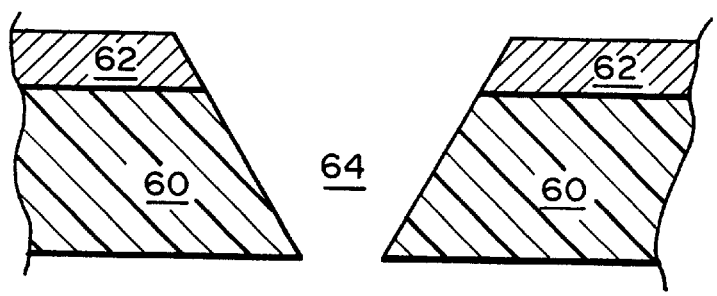
Figure 8C:
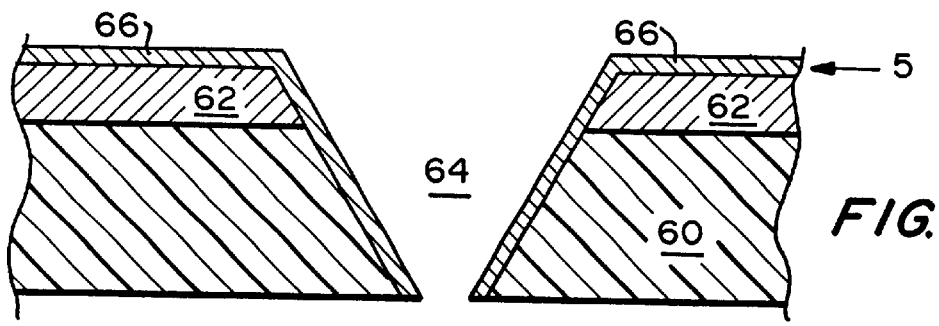
Figure 8D:
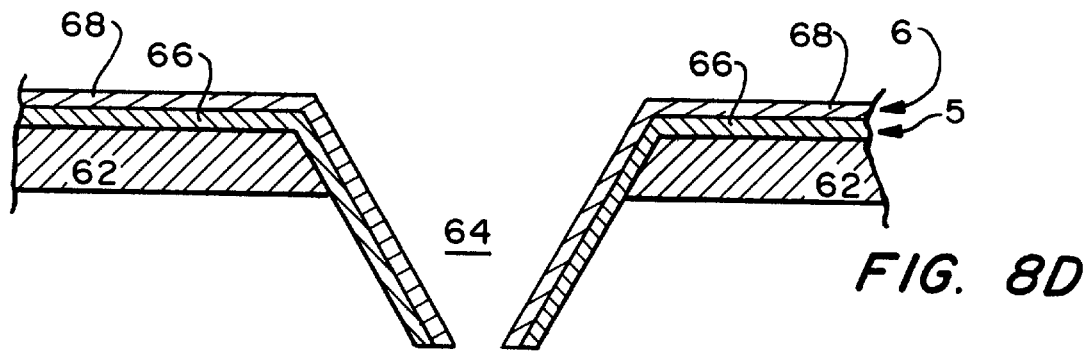

EXAMPLE 6
Micromold Fabrication of Tapered Microneedles Using Laser-Formed Molds A micromold having tapered walls was fabricated by use of laser ablation techniques, as shown in FIGS. 8a–d. A laser-ablatable polymer sheet 60 such as KAPTON™ polymide approximately 150 microns in thickness was optionally laminated to a thin (10–30 micron) metal sheet 62 such as titanium (FIG. 8a). A tapered bole 64 was formed in the metal/polymer laminate 60/62 using a laser technique such as excimer laser ablation (FIG. 8b). The entry hole of the laser spot was on the metal side 62, and a through hole was made through both the metal sheet and the polymer film. The through hole 64 was tapered in combination with either defocusing or appropriate substrate motion to create a taper such that the wide end of the hole 64 (typically 40–50 microns) was on the metal side 62 and the narrow end of the hole 64 (typically 10–20 microns) was on the polymer 60 side. A thin layer of metal 66, e.g. titanium, of thickness 0.1 micron was then deposited, e.g., using a sputter-deposition technique, in such a way that the metal 66 deposited on the metal film side and coated the polymer sidewalls, but did not coat the polymer 60 side of the laminate (FIG. 8c). Electrodeposition of metal 68, e.g., gold, to a thickness of 1–5 microns was then performed on the titanium-coated metal surface 66, and polymer sidewalls curved section of 60 next to 64. Finally, the polymer 60 was removed, using e.g. an oxygen plasma, to form the completed microneedles (FIG. 8d).

Alternate polymer removal methods, such as thermal, solvent, aqueous, or phodegradation followed by solvent or aqueous removal, are also possible if the polymer material is chosen appropriately (e.g., a photoresist resin).

EXAMPLE 7
Formation of Microneedles by Embossing

Figure 9A:
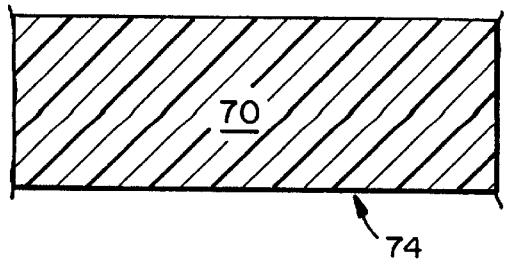
FIGS. 9a through 9f are side cross-sectional views illustrating a second method for making tapered microneedles using laser-formed molds.
Figure 9B:
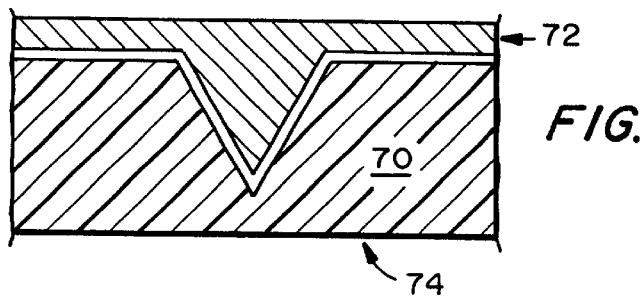
Figure 9C:
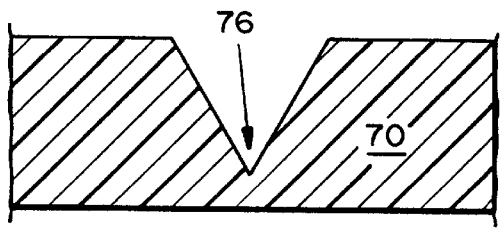
Figure 9D:
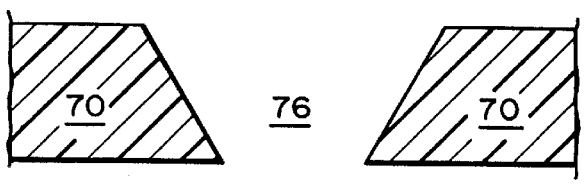
Figure 9E:
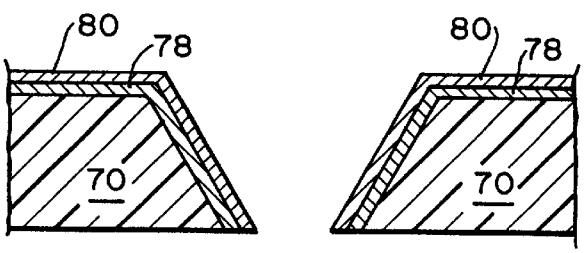
Figure 9F:
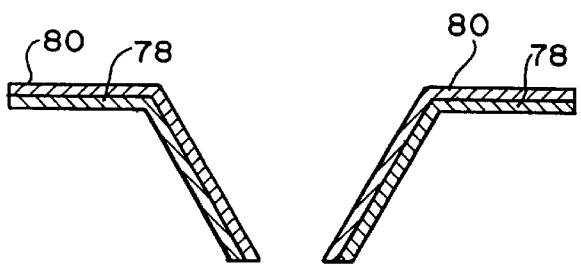

Formation of a microneedle by embossing is shown in FIGS. 9a–9f. A polymeric layer 70 (FIG. 9a) is embossed by a solid microneedle or microneedle array 72 (FIG. 9b). The array 72 is removed (FIG. 9c), and the layer 70 is etched from the non-embossed side 74 until the embossed cavity 76 is exposed (FIG. 9d). A metallic layer 78 is then deposited on the embossed side and the sidewalls, but not on the non-embossed side 74 (FIG. 9e). This layer 78 is optionally thickened by electrodeposition of an additional metal layer 80 on top of it (FIG. 9e). The polymer layer 70 is then removed to form the microneedles 78/80 (FIG. 9f).

EXAMPLE 8
Transdermal Application of Hollow Microneedles

The bore of hollow microneedles must provide fluid flow with minimal clogging in order to be suitable to transport material, such as in transdermal drug delivery. Therefore, microneedies and microtubes were evaluated to determine their suitability for these functions.

Hollow metal and silicon microneedles, produced as described in Examples 3–5, were inserted through human skin epidermis with no apparent clogging of the needle bores. Scanning electron microscopy of a hollow metal (NiFe) microneedle penetrating up through the underside of human epidermis showed the microneedle remains intact, with the tip free of debris. Similarly, silicon microneedles, metal microneedles, and metal microtubes were successfully inserted through human skin. Also, the hollow microneedles were shown to permit the flow of water through their bores.

EXAMPLE 9
Transport of Drugs through Microneedles Inserted into Skin

Studies were performed with solid and hollow microneedles to demonstrate transport of molecules and fluids. As shown in Table 1, transport of a number of different compounds across skin is possible using microneedles. These studies were performed using either solid silicon microneedles or using hollow silicon microneedles made by methods described in this patent. Transport was measured across human cadaver epidermis in vitro using Franz diffusion chambers at 37° C. using methods described in S. Henry, D. McAllister, M. G. Allen and M. R. Prausnitz. Microfabricated microneedles: A novel method to increase transdermal drug delivery. J. Pharm. Sci. 87, 922–925 (1998).

The transdermal delivery of calcein, insulin, bovine serum albumin and nanoparticles was measured. Delivery refers to the ability to transport these compounds from the stratum corneum side of the epidermis to the viable epidermis side. This is the direction of transport associated with delivering drugs into the body. Removal of calcein was also measured. Removal refers to the ability to transport calcein from the viable epidermis side of the epidermis to the stratum corneum side. This is the direction of transport associated with removing from the body compounds found in the body, such as glucose.

In all cases shown in Table 1, transport of these compounds across skin occurred at levels below our detection limit when no needles were inserted into the skin. Intact skin provides an excellent barrier to transport of these compounds. In all cases examined, when solid microneedles were inserted into the skin and left in place, large skin permeabilities were measured, indicating that the microneedles had created pathways for transport across the skin. Furthermore, in all cases, when solid microneedles were inserted into the skin and then removed, even greater skin permeabilities resulted. Finally, when hollow microneedles were inserted into the skin and left in place, still greater skin permeabilities resulted for those compounds tested. These studies show that microneedles can dramatically increase skin permeability and can thereby increase transport of a number of different compounds across the skin. It also shows that when solid microneedles are used, a preferred embodiment involves inserting and then removing microneedles, rather than leaving them in place. It also shows that using hollow microneedles are a preferred embodiment over the use of solid microneedles.

In Table 2, the flow rate of water through hollow silicon microneedles is shown as a function of applied pressure. These data demonstrate that significant flow rates of water through microneedles can be achieved at modest pressures.

TABLE 1

Transport of Drugs through Microneedles inserted into Skin.

| Compound | No needles | Solid needles inserted | Solid needles inserted and removed | Hollow needles inserted |
|---|---|---|---|---|
| Calcein delivery | ** | $4 \times 10^{-3}$ | $1 \times 10^{-2}$ | $1 \times 10^{-1}$ |
| Calcein removal | ** | $2 \times 10^{-3}$ | $1 \times 10^{-2}$ | n.a. |
| Insulin delivery | ** | $1 \times 10^{-4}$ | $1 \times 10^{-2}$ | n.a. |
| Bovine serum albumin delivery | ** | $9 \times 10^{-4}$ | $8 \times 10^{-3}$ | $9 \times 10^{-2}$ |
| Nanoparticle delivery | ** | n.a. | $3 \times 10^{-5}$ | n.a. |

**means that the transport was below the detection limit.
n.a. means that the data are not available.
Nanoparticles were made of latex with a diameter of approximately 100 nm.

TABLE 2

Flow rate of water through hollow silicon microneedles as a function of applied pressure

| Pressure (psi) | Flow rate (ml/min) |
|---|---|
| 1.0 | 16 |
| 1.5 | 24 |
| 2.0 | 31 |
| 2.5 | 38 |
| 3.0 | 45 |

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for making a microneedle device having a substrate to which a plurality of microneedles are attached or integrally formed, the method comprising
   (i) forming a micromold having sidewalls which define a surface of each of the microneedles; and
   (ii) using the micromold to form the microneedles and the substrate, wherein the microneedles extend at an angle from the substrate.

2. The method of claim 1 wherein the micromold is formed by a process which includes providing a mold substrate and then forming a plurality of holes in the mold substrate, thereby forming the micromold wherein the inner surfaces of the holes define the sidewalls which correspond to outer surfaces of each of the microneedles.

3. The method of claim 2 wherein the holes are photolithographically defined.

4. The method of claim 2 wherein the holes are defined using a laser technique.

5. The method of claim 4 wherein the laser technique is laser ablation.

6. The method of claim 1 comprising, in step (ii), applying a metal, or other material having different properties than the material forming the micromold, to the sidewalls to form hollow microneedles, and then removing the micromold from the microneedles.

7. The method of claim 6 wherein the metal or other material is applied by a sputter-deposition technique or a electrodeposition technique.

8. The method of claim 6 wherein the micromold is removed using a process selected from the group consisting of oxygen plasma, thermal, solvent, aqueous, and photodegradation removal techniques.

9. The method of claim 6 wherein the metal or other material is applied by electroless plating.

10. The method of claim 1 comprising, in step (ii), filling the micromold with a fluid material that is hardened in the micromold to form the microneedles.

11. The method of claim 10 which utilizes injection molding or reaction injection molding.

12. The method of claim 1 wherein, in step (i), the micromold is fabricated by forming a mold from a mold-insert.

13. The method of claim 12 wherein the mold insert is an array of microneedles.

14. The method of claim 13 for forming hollow microneedles, comprising the steps of
 (a) layering a removable material onto the array to cover the microneedles of the mold-insert,
 (b) removing a part of the layer of removable material to expose the tips of the microneedles of the mold-insert, and
 (c) removing the mold-insert to yield a micromold.

15. The method of claim 14 further comprising
 (d) applying a metal, or other material having properties distinct from the material forming the micromold, onto the micromold to form the microneedles, and
 (e) removing the micromold from the microneedles.

16. The method of claim 14 wherein the micromold is removed using a process selected from the group consisting of oxygen plasma, thermal, solvent, aqueous, and photodegradation removal techniques.

17. The method of claim 1 wherein the micromold is shaped by embossing.

18. The method of 1 wherein the micromold is shaped using a laser to selectively remove material.

19. The method of claim 18 wherein the material is a polymer/metal laminante.

20. The method of claim 1 wherein the angle is about 90°.

21. The method of claim 2 wherein the microneedle is formed of a metal selected from the group consisting of nickel, iron, gold, titanium, copper, platinum, palladium, stainless steels, and alloys thereof.

22. The method of claim 1 wherein the micromold is formed of a polymeric material.

23. The method of claim 1 wherein the microneedles comprise a polymer.

24. The method of claim 1 wherein the micromold formed in step (i) is in the form of an array of mold microneedles, wherein the outer surfaces of each of the mold microneedles correspond to the sidewalls which define the inner surface of hollow microneedles; and
 wherein, in step (ii), the array is coated with a material forming the microneedles and the substrate of the device, and then the micromold is removed.

* * * * *

UNITED STATES PATENT AND TRADEMARK OFFICE
CERTIFICATE OF CORRECTION

PATENT NO. : 6,334,856 B1
DATED : January 1, 2002
INVENTOR(S) : Allen et al.

It is certified that error appears in the above-identified patent and that said Letters Patent is hereby corrected as shown below:

<u>Title page,</u>
Item [63], delete ", now Pat. No. 6,193,700".

<u>Column 1,</u>
Line 7, delete "now U.S. Pat. No. 6,193,700."

<u>Column 26,</u>
Line 19, delete "laminante" and insert -- laminate --.
Line 21, delete "2" and insert -- 1 --.

Signed and Sealed this

Thirteenth Day of August, 2002

*Attest:*

*Attesting Officer*

JAMES E. ROGAN
*Director of the United States Patent and Trademark Office*